US009010309B2

(12) United States Patent
Lewis et al.

(10) Patent No.: US 9,010,309 B2
(45) Date of Patent: Apr. 21, 2015

(54) BALL THROWING MACHINE AND METHOD

(75) Inventors: Edward J. Lewis, Thousand Oaks, CA (US); Steven Joseph Barberi, Mission Viejo, CA (US)

(73) Assignee: Toca, LLC, Thousand Oaks, CA (US)

(*) Notice: Subject to any disclaimer, the term of this patent is extended or adjusted under 35 U.S.C. 154(b) by 477 days.

(21) Appl. No.: 13/287,749

(22) Filed: Nov. 2, 2011

(65) Prior Publication Data

US 2013/0104869 A1    May 2, 2013

(51) Int. Cl.
*A63B 69/40* (2006.01)
*A63B 65/12* (2006.01)
*F41B 4/00* (2006.01)
(Continued)

(52) U.S. Cl.
CPC ............... *A63B 69/002* (2013.01); *A63B 69/40* (2013.01); *A63B 71/0619* (2013.01); *A63B 24/0075* (2013.01); *G09B 19/0038* (2013.01); *A63B 69/406* (2013.01); *A63B 2243/0025* (2013.01); *A63B 2069/402* (2013.01); *A63B 2208/12* (2013.01); *A63B 2225/50* (2013.01); *A63B 2071/063* (2013.01); *A63B 2071/0677* (2013.01); *A63B 2071/068* (2013.01); *A63B 2071/0683* (2013.01); *A63B 2220/56* (2013.01); *A63B 2220/801* (2013.01); *A63B 2220/806* (2013.01); *A63B 2220/836* (2013.01); *A63B 2225/20* (2013.01); *A63B 2230/062* (2013.01); *A63B 2243/0004* (2013.01); *A63B 2243/0008* (2013.01); *A63B 2243/0016* (2013.01); *A63B 2243/005* (2013.01); *A63B 2243/0075* (2013.01); *A63B 2243/0079* (2013.01); *A63B 2243/0083* (2013.01); *A63B 2243/0095* (2013.01)

(58) Field of Classification Search
CPC .................. A63B 69/406; A63B 69/40; A63B 2069/402; A63B 2243/0025; G09B 19/0038
USPC .............. 124/4, 6, 8, 9, 78, 81; 473/422, 446; 700/91
See application file for complete search history.

(56) References Cited

U.S. PATENT DOCUMENTS 2,918,915 A    12/1959    Doeg
3,028,704 A    4/1962    Rumbaugh
(Continued)

FOREIGN PATENT DOCUMENTS

CA    2676348    2/2011
EP    0400325    4/1990
WO    WO 2006/081702    8/2006

OTHER PUBLICATIONS

International Search Report and Written Opinion issued in application No. PCT/US2013/039143 on Nov. 1, 2013.
(Continued)

*Primary Examiner* — Melba Bumgarner
*Assistant Examiner* — Alexander Niconovich
(74) *Attorney, Agent, or Firm* — Knobbe Martens Olson & Bear LLP

(57) ABSTRACT

A ball throwing machine can include a hopper for receiving one or more balls and a ball delivery device. The ball delivery device can be used to throw or pitch a ball from the hopper to a user of the machine. The ball delivery device can include wheels to impart speed to the ball and a direction system to control the projection angle of the ball. The direction system can control at least one of the up and down angle and the side to side angle of the ball as it is thrown, among possibly other throwing parameters. A controller may be provided for controlling operation of the ball throwing machine.

27 Claims, 17 Drawing Sheets

(51) Int. Cl.
  *G09B 19/00* (2006.01)
  *A63B 69/00* (2006.01)
  *A63B 71/06* (2006.01)
  *A63B 24/00* (2006.01)

(56) References Cited

U.S. PATENT DOCUMENTS

| | | | |
|---|---|---|---|
| 3,272,194 A | 9/1966 | Egbert | |
| 3,306,613 A | 2/1967 | Mainers | |
| 3,459,168 A | 8/1969 | Bruce | |
| 3,470,859 A | 10/1969 | Ponza | |
| 3,570,466 A | 3/1971 | White et al. | |
| 3,659,576 A | 5/1972 | Eade et al. | |
| 3,677,544 A | 7/1972 | Meyers et al. | |
| 3,777,732 A | 12/1973 | Holloway et al. | |
| 3,779,227 A | 12/1973 | Scott | |
| 3,785,358 A | 1/1974 | D'angelo et al. | |
| 3,794,011 A | 2/1974 | Newgarden, Jr. | |
| 3,815,567 A | 6/1974 | Serra | |
| 3,844,267 A | 10/1974 | Mohr | |
| 3,855,988 A | 12/1974 | Sweeton | |
| 3,892,217 A | 7/1975 | Raty | |
| 3,913,552 A | 10/1975 | Yarur et al. | |
| 3,930,486 A | 1/1976 | Kahelin | |
| 3,990,426 A | 11/1976 | Stokes | |
| 4,025,071 A | 5/1977 | Hodges | |
| 4,046,131 A | 9/1977 | Clark et al. | |
| 4,077,386 A | 3/1978 | Berliner | |
| 4,086,903 A | 5/1978 | Scott | |
| 4,094,294 A | 6/1978 | Speer | |
| 4,209,003 A | 6/1980 | Sainsbury | |
| 4,209,004 A | 6/1980 | Kennedy | |
| 4,262,648 A | 4/1981 | Wegener et al. | |
| 4,280,697 A | 7/1981 | Yuasa | |
| 4,282,848 A | 8/1981 | Kulesza et al. | |
| 4,299,383 A | 11/1981 | Yuasa | |
| 4,323,047 A | 4/1982 | Mcintosh et al. | |
| 4,352,348 A * | 10/1982 | Griffith | 124/78 |
| 4,409,953 A | 10/1983 | Kennedy et al. | |
| 4,423,717 A | 1/1984 | Kahelin | |
| 4,442,823 A * | 4/1984 | Floyd et al. | 124/78 |
| 4,524,749 A | 6/1985 | Giovagnoli | |
| 4,531,504 A | 7/1985 | Gilreath | |
| 4,559,918 A | 12/1985 | Ballerin et al. | |
| 4,563,999 A | 1/1986 | Miehlich | |
| 4,596,230 A | 6/1986 | Griffith | |
| 4,632,088 A | 12/1986 | Bruce | |
| 4,646,709 A * | 3/1987 | Kholin | 124/82 |
| 4,655,190 A | 4/1987 | Harris | |
| 4,669,444 A | 6/1987 | Whitfield et al. | |
| 4,723,532 A | 2/1988 | Osojnak | |
| 4,765,618 A | 8/1988 | Daley | |
| 4,772,017 A | 9/1988 | Eriksen | |
| 4,823,763 A | 4/1989 | Ponza | |
| 4,834,060 A | 5/1989 | Greene | |
| 4,875,459 A | 10/1989 | Van Elderen et al. | |
| 4,896,646 A | 1/1990 | Kahelin et al. | |
| 4,907,802 A | 3/1990 | Gatin | |
| 4,922,885 A | 5/1990 | Iwabuchi et al. | |
| 5,012,790 A | 5/1991 | Bates | |
| 5,044,350 A | 9/1991 | Iwabuchi et al. | |
| 5,097,985 A | 3/1992 | Jones | |
| 5,107,820 A | 4/1992 | Salansky | |
| 5,121,735 A | 6/1992 | Hancock | |
| 5,125,653 A * | 6/1992 | Kovacs et al. | 124/78 |
| 5,174,565 A | 12/1992 | Komori | |
| 5,181,501 A | 1/1993 | Lien | |
| 5,347,975 A | 9/1994 | Salansky | |
| 5,359,986 A | 11/1994 | Magrath, III et al. | |
| 5,396,876 A * | 3/1995 | Liscio et al. | 124/6 |
| 5,464,208 A * | 11/1995 | Pierce | 473/451 |
| 5,490,493 A * | 2/1996 | Salansky | 124/78 |
| 5,496,025 A | 3/1996 | Phillips et al. | |
| 5,607,151 A | 3/1997 | Daley | |
| 5,649,523 A | 7/1997 | Scott | |
| 5,722,384 A | 3/1998 | Cox | |
| 5,865,161 A | 2/1999 | Bruce | |
| 5,897,445 A * | 4/1999 | Sanders | 473/421 |
| 5,911,214 A * | 6/1999 | Andrews | 124/16 |
| 5,979,426 A | 11/1999 | Troklus et al. | |
| 6,026,798 A * | 2/2000 | Sanders et al. | 124/78 |
| 6,186,132 B1 * | 2/2001 | Ko | 124/6 |
| 6,190,271 B1 | 2/2001 | Rappaport et al. | |
| 6,224,503 B1 * | 5/2001 | Joseph | 473/422 |
| 6,237,583 B1 | 5/2001 | Ripley et al. | |
| 6,401,704 B1 | 6/2002 | Caldwell | |
| 6,402,640 B1 | 6/2002 | Stuart | |
| 6,427,675 B1 | 8/2002 | Caldwell et al. | |
| 6,443,859 B1 | 9/2002 | Markin | |
| 6,470,873 B2 * | 10/2002 | Battersby et al. | 124/78 |
| 6,488,020 B1 * | 12/2002 | Rosas-Magallan | 124/78 |
| 6,508,243 B1 | 1/2003 | Long | |
| 6,513,512 B2 * | 2/2003 | Battersby et al. | 124/78 |
| 6,539,931 B2 * | 4/2003 | Trajkovic et al. | 124/34 |
| 6,546,924 B2 * | 4/2003 | Battersby et al. | 124/78 |
| 6,637,422 B2 | 10/2003 | Wojtkiewicz et al. | |
| 6,857,424 B1 | 2/2005 | Payne | |
| 6,877,501 B2 | 4/2005 | Wojtkiewicz et al. | |
| 6,880,542 B1 * | 4/2005 | Johndreau et al. | 124/78 |
| 7,011,084 B2 | 3/2006 | Richard | |
| 7,032,585 B2 | 4/2006 | Johndreau et al. | |
| 7,040,309 B2 | 5/2006 | Johndreau et al. | |
| 7,056,237 B2 | 6/2006 | Slavey et al. | |
| 7,066,845 B2 | 6/2006 | Joseph | |
| 7,082,938 B2 * | 8/2006 | Wilmot | 124/78 |
| 7,100,594 B2 | 9/2006 | Boehner | |
| 7,111,620 B2 | 9/2006 | Johndreau et al. | |
| 7,231,913 B2 | 6/2007 | Wilson | |
| 7,237,546 B2 | 7/2007 | Nozato | |
| 7,258,633 B2 | 8/2007 | Joseph et al. | |
| 7,278,934 B2 | 10/2007 | Mcbride et al. | |
| 7,285,061 B2 * | 10/2007 | Wagner | 473/459 |
| 7,290,540 B2 | 11/2007 | Lu et al. | |
| 7,445,003 B2 | 11/2008 | Smith | |
| 7,510,493 B2 * | 3/2009 | Wagner | 473/459 |
| 7,527,568 B2 | 5/2009 | Joseph | |
| 7,549,415 B2 * | 6/2009 | Karellas | 124/16 |
| 7,553,244 B2 | 6/2009 | York | |
| 7,610,909 B2 * | 11/2009 | Greene, Jr. | 124/78 |
| 7,691,012 B2 * | 4/2010 | Cucjen et al. | 473/422 |
| 7,708,003 B2 | 5/2010 | Gavieres | |
| 7,766,770 B2 * | 8/2010 | Cucjen et al. | 473/422 |
| 7,806,788 B1 | 10/2010 | Neuman | |
| 7,861,699 B2 * | 1/2011 | Gowan et al. | 124/32 |
| 7,882,831 B2 * | 2/2011 | Alger | 124/78 |
| 8,206,246 B2 * | 6/2012 | Joseph et al. | 473/433 |
| 8,287,404 B2 * | 10/2012 | Cucjen et al. | 473/422 |
| 8,342,162 B2 * | 1/2013 | Alger | 124/78 |
| 8,480,517 B2 * | 7/2013 | Guttler | 473/446 |
| 8,517,870 B2 | 8/2013 | Crowley et al. | |
| 8,540,560 B2 * | 9/2013 | Crowley et al. | 463/4 |
| 8,550,063 B2 * | 10/2013 | Alger | 124/78 |
| 8,579,632 B2 * | 11/2013 | Crowley | 434/247 |
| 8,597,095 B2 * | 12/2013 | Crowley et al. | 463/4 |
| 2004/0176192 A1 | 9/2004 | Slavey et al. | |
| 2005/0085320 A1 | 4/2005 | Joseph et al. | |
| 2005/0209027 A1 | 9/2005 | Joseph | |
| 2006/0042611 A1 * | 3/2006 | Karellas | 124/16 |
| 2006/0118096 A1 * | 6/2006 | Cucjen et al. | 124/78 |
| 2006/0135290 A1 | 6/2006 | Lin | |
| 2006/0236993 A1 * | 10/2006 | Cucjen et al. | 124/78 |
| 2008/0058128 A1 | 3/2008 | Joseph | |
| 2009/0095273 A1 | 4/2009 | Paulson et al. | |
| 2009/0210078 A1 * | 8/2009 | Crowley | 700/91 |
| 2010/0252015 A1 * | 10/2010 | Cucjen et al. | 124/78 |
| 2010/0261557 A1 | 10/2010 | Joseph et al. | |
| 2011/0073091 A1 * | 3/2011 | Gowan et al. | 124/26 |
| 2011/0230273 A1 * | 9/2011 | Niegowski et al. | 473/199 |
| 2011/0303207 A1 * | 12/2011 | Shober et al. | 124/54 |
| 2012/0029666 A1 * | 2/2012 | Crowley et al. | 700/91 |
| 2012/0058845 A1 | 3/2012 | Crowley et al. | |
| 2013/0005512 A1 | 1/2013 | Joseph et al. | |

(56) References Cited

U.S. PATENT DOCUMENTS

| | | |
|---|---|---|
| 2013/0079906 A1 | 3/2013 | Crowley et al. |
| 2013/0157786 A1 | 6/2013 | Joseph et al. |
| 2014/0031151 A1 | 1/2014 | Crowley et al. |
| 2014/0039651 A1 | 2/2014 | Crowley |
| 2014/0081436 A1 | 3/2014 | Crowley et al. |

OTHER PUBLICATIONS

Slash Gear webpage, Adidas miCoach Smart Ball connects soccer to smartphone, http://www.slashgear.com/adidas-micoach-smart-ball-connects-soccer-to-smartphone-27330732/, last accessed on Jun. 3, 2014.

* cited by examiner

FIG. 17

BALL THROWING MACHINE AND METHOD

BACKGROUND

In soccer, to be in control of the ball is of importance to every level of player. The ability to control an awkward bouncing ball quickly and effectively gives the player with the ball the immediate advantage. First touch is often the difference between success and failure in most situations during the match.

As players get older, the game gets faster and demands more speed. Consequently, there is a greater need for first-time passes and a precise first touch on the ball. Often, players cannot always play a first-time ball; therefore, they must trap the ball or may have to dribble if no teammates are in position to receive a first-time pass. A player will typically do one of four things when controlling the ball: shield the ball by putting their body between the ball and the opponent, pass the ball, shoot the ball, or dribble the ball. The space and time a player has to do these things can depend on how good the player's first touch is when receiving the ball.

Players can improve by developing a better touch or feel for the ball. A fine touch enables a player to be comfortable touching the ball with all parts of the foot as well as other parts of the body. It is helpful for players to practice controlling balls on the ground and balls in the air. Good ball control involves the ability to take the ball with one touch in such a way that a player can play the ball with his next movement without having to chase or reach for it.

SUMMARY

In certain embodiments, a soccer ball throwing device includes a hopper that can hold a plurality of soccer balls and a ball delivery device that can receive the soccer balls from the hopper. The ball delivery device can include one or more wheels that can impart motion to one of the soccer balls and a frame attached to the one or more wheels. The frame can be positionable to control a trajectory of the ball. The soccer ball throwing device may also include a ball delivery control circuit that can control the position of the frame and the speed of the one or more wheels. Further, the ball throwing device can include a controller in communication with the ball delivery control circuit. The controller can include one or more processors that can at least: cause the soccer ball throwing device to perform an initial training program that includes a set of one or more ball trapping drills, where the controller causes the soccer ball throwing device to pitch one or more of the soccer balls to a player during said one or more ball trapping drills, enabling the player to practice trapping the ball and thereby improve ball control skills; record player training data that includes information regarding training of the player performed during the initial training program; submit the player training data from the controller over a network to a soccer network application along with a request for feedback from a remote coach through the soccer network application; and in response to submission of the training session data, receive a customized training program from the coach via the soccer network application. The customized training program can include one or more second drills to be executed by the soccer ball throwing device.

In various embodiments, a method of controlling a soccer ball throwing device includes providing a soccer ball throwing device having a hopper that can hold a plurality of soccer balls, a ball delivery device that can receive the soccer balls from the hopper, where the ball delivery device has one or more wheels that can impart motion to one of the soccer balls, and a frame attached to the one or more wheels, where the frame is positionable to control a trajectory of the ball, and a ball delivery control circuit that can control the position of the frame and the speed of the one or more wheels. The method can also include communicating with the soccer ball throwing device via a controller including computer hardware. The method may also include causing the soccer ball throwing device, with the controller, to perform an initial training program that comprises a set of one or more ball trapping drills, where the controller causes the soccer ball throwing device to pitch one or more balls to a player during said one or more ball trapping drills, enabling the player to practice trapping the ball and thereby improve ball control skills. Moreover, the method can include recording player training data that includes information regarding training of the player performed during the initial training program, submitting the player training data from the controller over a network to a soccer network application along with a request for feedback from a remote coach through the soccer network application, and in response to said submitting the training session data, receiving a customized training program from the coach via the soccer network application. The customized training program can include one or more second drills to be executed by the soccer ball throwing device. The method can be implemented by one or more physical processors.

A method of controlling a soccer ball throwing device can include, in various embodiments, establishing communication between a soccer ball throwing device and a controller having computer hardware. The method can also include causing the soccer ball throwing device, with the controller, to perform an initial training program that comprises a set of one or more ball trapping drills, where the controller causes the soccer ball throwing device to pitch one or more balls to a player during said one or more ball trapping drills, enabling the player to practice trapping the ball and thereby improve ball control skills. The method can also include recording player training data that includes information regarding training of the player performed during the initial training program. Further, the method can include submitting the player training data from the controller over a network to a soccer network application along with a request for feedback from a remote coach through the soccer network application, and in response to submitting the training session data, receiving a customized training program from the coach via the soccer network application. The customized training program can include one or more second drills to be executed by the soccer ball throwing device. The method can also be implemented by one or more physical processors.

A system for controlling a ball throwing device can include a ball machine control module that can cause a soccer ball throwing device to perform an initial training program that includes a set of one or more ball trapping drills. The ball machine control module causes the soccer ball throwing device to pitch one or more balls to a player during said one or more ball trapping drills in certain embodiments, enabling the player to practice trapping the ball and thereby improve ball control skills. The system can also include a training module implemented in one or more processors. The training module can record player training data that includes information regarding training of the player performed during the initial training program, submit the player training data over a network to a soccer network application along with a request for feedback from a remote coach through the soccer network application, and in response to said submitting the training session data, receive a customized training program from the coach via the soccer network application. The customized training program can include one or more second drills to be executed by the soccer ball throwing device.

In some embodiments, non-transitory physical computer storage is provided that includes instructions stored therein for implementing, in one or more processors, a system for controlling a ball throwing device. The system can include a ball machine control module that can cause a soccer ball throwing device to perform an initial training program that includes a set of one or more ball trapping drills. The ball machine control module can cause the soccer ball throwing device to pitch one or more balls to a player during said one or more ball trapping drills, enabling the player to practice trapping the ball and thereby improve ball control skills. The system can also include a training module that can record player training data that includes information regarding training of the player performed during the initial training program, submit the player training data over a network to a soccer network application along with a request for feedback from a remote coach through the soccer network application, and in response to submitting the training session data, receive a customized training program from the coach via the soccer network application. The customized training program can include one or more second drills to be executed by the soccer ball throwing device.

A method of controlling ball throwing devices can include, in some embodiments, receiving player training data from a plurality of controllers of ball throwing machines. The player training data can correspond to a plurality of players. In addition, the player training data can reflect usage by the players of the ball throwing machines. The method may also include electronically generating a remote coaching user interface by a computer system including computer hardware. The remote coaching user interface can include options for the coach to select recommended training programs for the players based on the player training data. The method can also include receiving, from the remote coaching user interface, coach-selected training programs to be sent to the plurality of controllers. Moreover, the method can include providing data representing the selected training programs to the plurality of controllers, thereby enabling the players to implement the selected training programs in the respective ball throwing machines of the players.

Certain aspects, advantages and novel features of the inventions are described herein. It is to be understood that not necessarily all such advantages may be achieved in accordance with any particular embodiment of the inventions disclosed herein. Thus, the inventions disclosed herein may be embodied or carried out in a manner that achieves or selects one advantage or group of advantages as taught herein without necessarily achieving other advantages as may be taught or suggested herein.

BRIEF DESCRIPTION OF THE DRAWINGS

The features disclosed herein are described below with reference to the drawings. Throughout the drawings, reference numbers are re-used to indicate correspondence between referenced elements. The drawings are provided to illustrate embodiments of the inventions described herein and not to limit the scope thereof.

FIGS. 16 and 17 illustrate embodiments of user interfaces that may be generated by the soccer network application of FIG. 7.

DETAILED DESCRIPTION

I. Introduction

Figure 1:
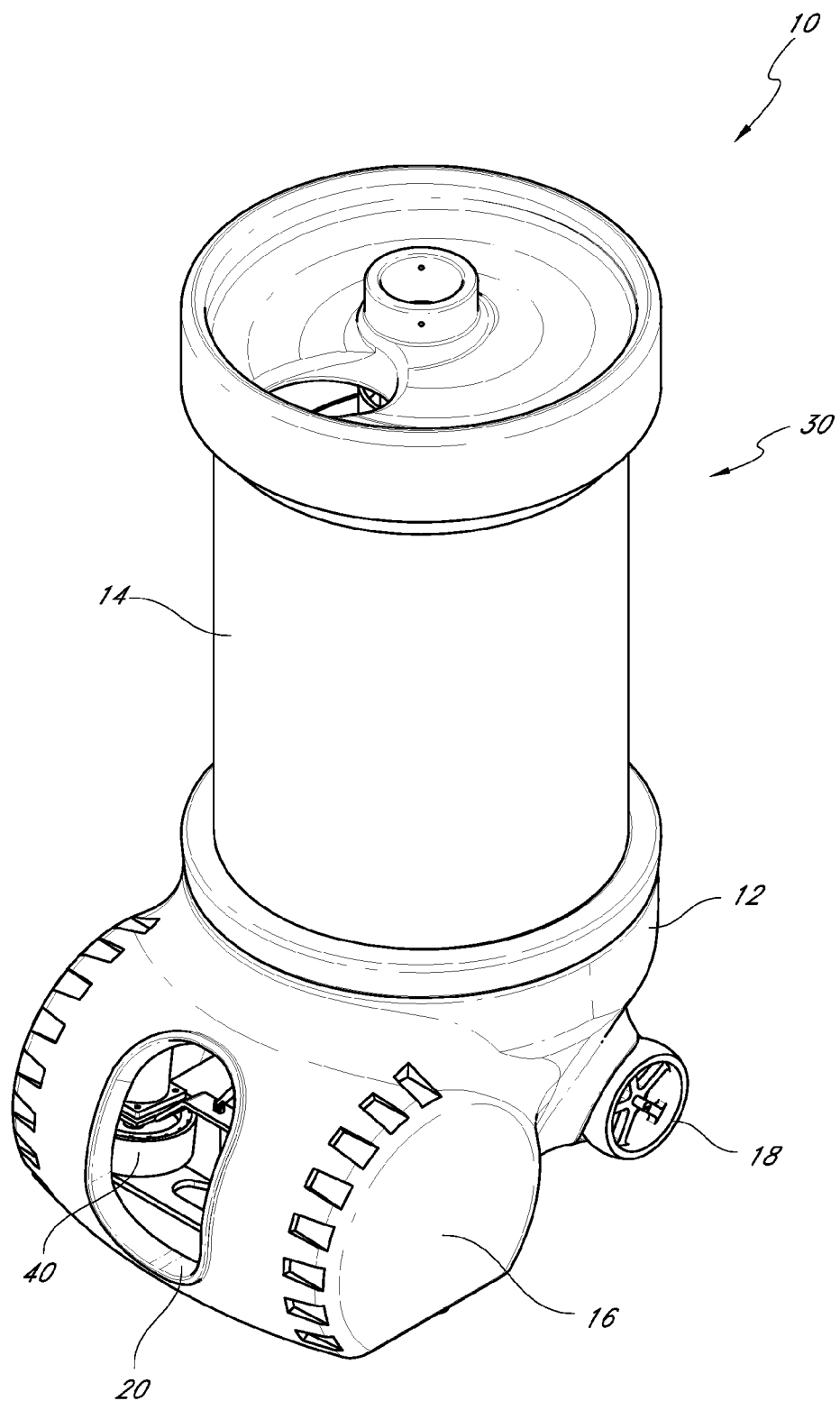
FIG. 1 is a perspective view of a ball throwing machine.

As described above, a soccer player's first touch of the ball is an important core skill to develop. A touch can be as simple as receiving a slow pass on the ground or as difficult as taking a top speed knuckling ball out of the air and straight down onto one's foot. Touch enhancement is a continual process; youth and professionals alike perpetually train to ever improve their first touch and ball handling skills. The skill of touch is typically trained by players forming pairs and passing the ball to one another. This training method can produce results but tends to fall short in providing a disciplined approach to training that enables progress measurement and goal-oriented improvement. Further, this technique requires a player to find another individual with which to practice, which is not always practical, particularly for serious athletes who devote significant time to their training.

This disclosure describes a specialized ball throwing machine that can be used to improve a player's first touch and ball control, among other benefits. The ball throwing machine can be designed to throw, lob, pitch, or otherwise eject soccer balls toward a player, who can trap the balls or practice other ball control skills. The ball throwing machine may be controlled using a controller in the form of a handheld computing device or the like. The controller can include software and hardware that enables the player to remotely control the machine, for example, wirelessly. The controller can include functionality for recording a player's progress with ball training, and the player can upload this progress information to a software network application, which may be a web site or the like. The soccer network application can provide functionality for a remote coach to analyze the player's progress and provide a customized training program to the player based on the player's progress. As a result, the ball throwing machine can enable the player to track progress and receive remote coaching to improve that progress. These and other features of the ball throwing machine, controller, and associated soccer network application are described in detail below.

The game of soccer is commonly known in some countries as "football" or "association football." For convenience, this specification refers solely to the term "soccer," although such usage should be considered synonymous with "football" and "association football." Further, embodiments of the ball throwing machine, controller, and soccer network application described herein can be used or adapted for sports other than soccer, some examples of which are described below.

It should also be noted that although this specification refers primarily to using a ball throwing machine to train ball trapping skills, the ball throwing machine can be used to train other skills. For example, the ball throwing machine can be used to train passing, shooting, and stopping a soccer ball, among other ball skills.

II. Example Ball Throwing Machine

A ball throwing machine 10 is shown in FIG. 1. The ball throwing machine 10 can be used to pitch a ball, such as to deliver a ball to a user. For example, the ball throwing machine 10 can be used to deliver a soccer ball or a specialized soccer-type ball to a user. The ball throwing machine 10 can also be used with various other balls for various other sports.

The illustrated ball throwing machine 10 includes an outer housing 12 with an upper section 14 and a lower section 16. The ball throwing machine 10 can be that can be easily movable. For example, the ball throwing machine can include one or more motorized wheels 18. Some embodiments may also include one or more handles for securing the ball throwing machine while moving the same.

Figure 2:
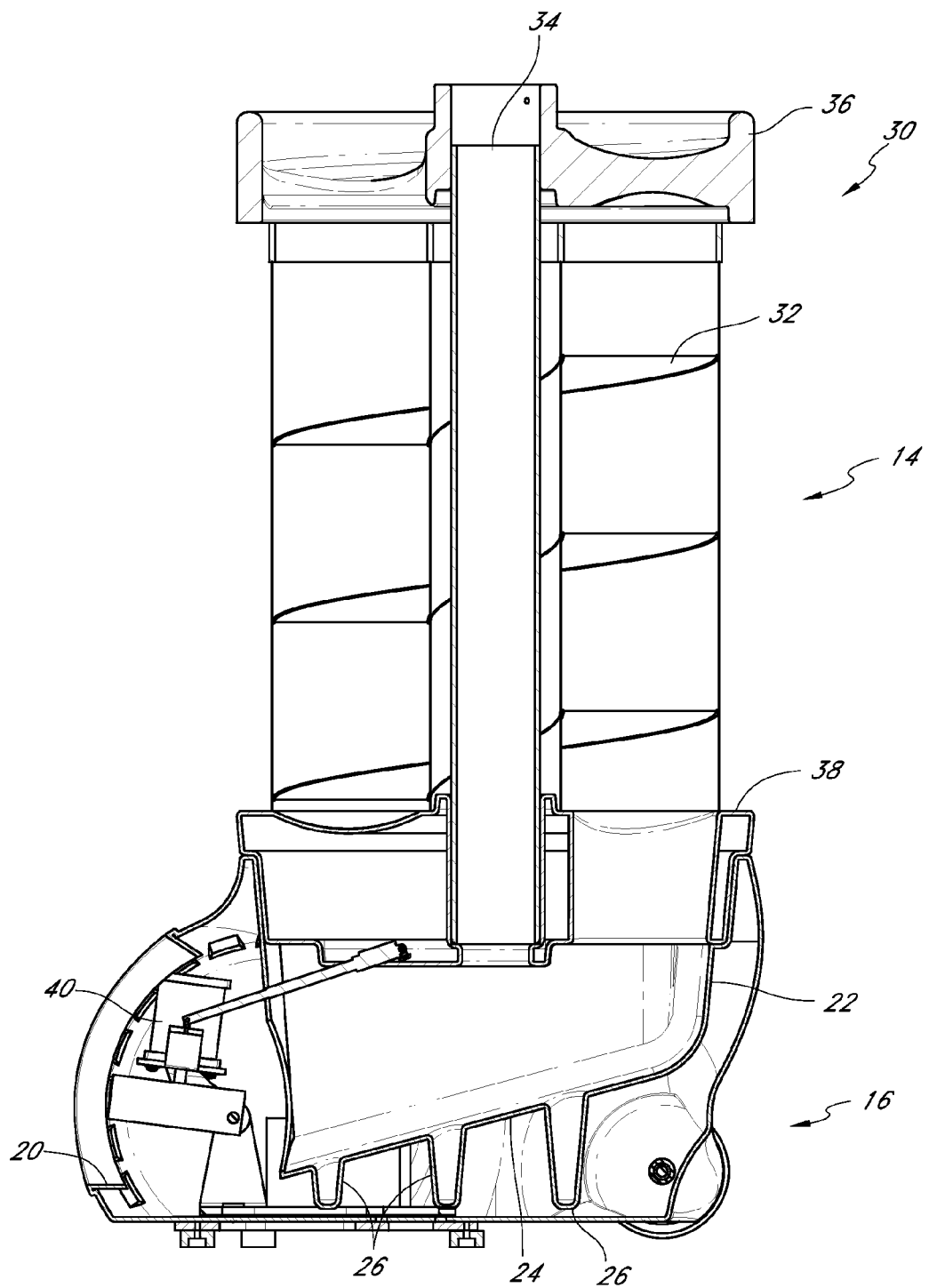
FIG. 2 is a cross-section of the ball throwing machine of FIG. 1.

As can be seen in FIGS. 1 and 2, the upper section 14 includes a hopper 30. The hopper 30 can be used to receive and/or store balls to later be ejected or thrown by the ball throwing machine 10. The illustrated embodiment includes a high-volume or large storage-type hopper 30. In some embodiments, the hopper can store as many as 25 balls. Of course, it will be understood that the hopper could hold more or less balls, as necessary or desired.

Many different styles and types of hoppers can be used. As shown, the hopper 30 is a gravity-type hopper with a spiraling ramp 32 located around and internal tube 34. The tube 34 can be used to impart structural strength to the hopper an can also provide appropriate spacing such that balls within the hopper are able to properly rotate and move downward in the hopper. Alternatively, the tube 34 is not included in some embodiments. Rather, the hopper 30 merely includes the spiraling ramp 32. In another embodiment, the spiraling ramp 32 is omitted and the hopper 30 includes a tube 34 that holds a plurality of balls.

In some embodiments, the hopper 30 can be transparent. For example, the outer material of the hopper may be clear Plexiglas or plastic, or a thin mesh-like fabric. This transparency can allow the user to view the balls in the hopper 30 and identify when the hopper 30 needs to be reloaded. The hopper 30 can have a top portion 36 and a bottom portion 38. The top portion 36 can be configured for receiving one or more balls into the hopper 30 and in some embodiments, can hold additional balls. The bottom portion can be configured to transition balls from the hopper 30 into a ball staging area 42.

The hopper 30 can be used for storing balls when the ball throwing machine 10 is in use and/or when the ball throwing machine 10 is not in use. In some embodiments, the hopper 30 can be collapsible or detachable to decrease the size of the ball throwing machine 10, such as when the ball throwing machine is not in use. In some embodiments, the tube 34 can be a telescoping tube and the outer material of the hopper 30 can be fabric, such that the hopper 30 can increase or decrease in size. In some embodiments with the collapsible hopper 30, the top portion 36 can be collapsed to sit on top of the bottom portion 38. Alternatively, the tube 34 can be configured to be removable to remove structural support separating the top portion 36 from the bottom portion 38.

Advantageously, in certain embodiments, the ball throwing machine 10 is designed to deliver soccer balls that are smaller than adult regulation size soccer balls to thereby enable more effective training of ball trapping skills. The smaller surface area of such balls can make the smaller balls harder to trap than regulation size balls (such as size "5" soccer balls). Training with smaller balls can therefore benefit a player using a larger, regulation-size ball in a match because the player may have obtained skills that transfer over to the easier-to-trap, larger ball. In some embodiments, the balls used with the ball throwing machine 10 are about half the size of regulation size 5 balls, about a third of the size of regulation size 5 balls, about a quarter of the size of regulation size balls 5, or some other size. For youth players who may already be using a smaller ball than an adult ball in matches, the ball throwing machine 10 can employ even smaller balls than the youth players use in their matches. For instance, if youth player is used to using size 4 soccer balls, the ball throwing machine can throw size 3 soccer balls or smaller, etc. However, in other embodiments, regulation size balls are used instead of smaller balls.

The size of the balls used by the ball throwing machine 10 can be smaller than a regulation size 3 ball, even for older youth and adult players. For example, in one embodiment, the balls are preferably about 152 mm in diameter. However, in other embodiments the balls can range in size from about 132 mm to about 172 mm in diameter while still providing some or all of the benefits of the balls described herein. In still other embodiments, the balls can range in size from about 115 mm to 215 mm in diameter while still providing at least some of the benefits described herein.

A ball that may be used herein may have any of the following characteristics: a rubber construction, a butyl bladder, one or more nylon plys (such as 1, 2, 3, or 4 or more nylon plys), spiral winding of the nylon plys, and the like. These and other characteristics of the balls, among others (including size, texture, weight, cover type, etc.) can be selected to achieve a desired liveliness or bounciness of the ball. Different balls may be provided with different liveliness for different levels of difficulty. For instance, a ball that has more bounce may be harder to trap and thus appropriate for a higher level of difficulty, while a ball with less bounce may be easier to trap and thus appropriate for a lower level of difficulty.

Moreover, the colors of the balls can be selected to target foot-eye coordination. For example, the balls may be blue, green, or red, or a combination of the same, as these colors can be the easier to see than other colors. Alternatively, colors may be selected that are less easy to see so as to increase the difficulty of training. Different colors may be provided for boys and girls, who may perceive colors slightly differently.

In one embodiment, the balls are not actual soccer balls. For example, a ball having a smaller size than a regulation size ball can be considered to be a ball other than a soccer ball. Counterintuitively, it can be beneficial to train soccer skills (such as trapping) using balls that are not soccer balls, such as any of the balls described herein. Balls used in other sports can also be thrown by the ball throwing machine 10 for the purposes of training soccer skills. Tennis balls, racquet balls, and squash balls, for instance, can be beneficially used to train trapping skills.

Moving now to the bottom portion 16 of the outer housing 12, the bottom portion 16 is shown housing the ball staging area 42, as well as the ball delivery device 40. As can be seen in FIG. 2, the ball staging area 42 can include a ramp 24 that can hold one or more balls. The ramp 24 can include one or more ball stops 26. The ball stops can be used to stop individual balls or the balls collectively.

For example, as shown, the ball staging area 42 includes three ball stops 26. In some embodiments, the ball stops 26 can include a solenoid configured to advance and/or retract a rod or other member in front of a ball. The three balls stops 26 can allow the ball throwing machine 10 to control the projection of the ball completely with the ball delivery device 40. For example, separating the balls with multiple ball stops 26 can allow the ball delivery device 40 to pitch a ball without the influence of other balls acting or pushing upon the ball. It will be understood that the balls in the hopper may be pressing down on one another by gravity and could have an influencing effect on the trajectory of the ball, if allowed to contact the ball being pitched. However, fewer than three ball stops 26 may be included in the machine 10 instead.

As is shown, the bottom portion 16 of the outer housing also includes at least one opening 20. The opening 20 can provide space for the ball to be thrown through to the user. The opening 20 can be one of many different shapes, such as oval, elliptical, rectangular, triangular, or any other desired shape. In some embodiments, the bottom portion 16 of the outer housing 12 includes a minimal amount of material, such that a majority, or at least a substantial portion, of the ball delivery device 40 is exposed and not enclosed. In such embodiments, little to no portion of the outer housing may be between the ball delivery device 40 and the user.

Figure 3:
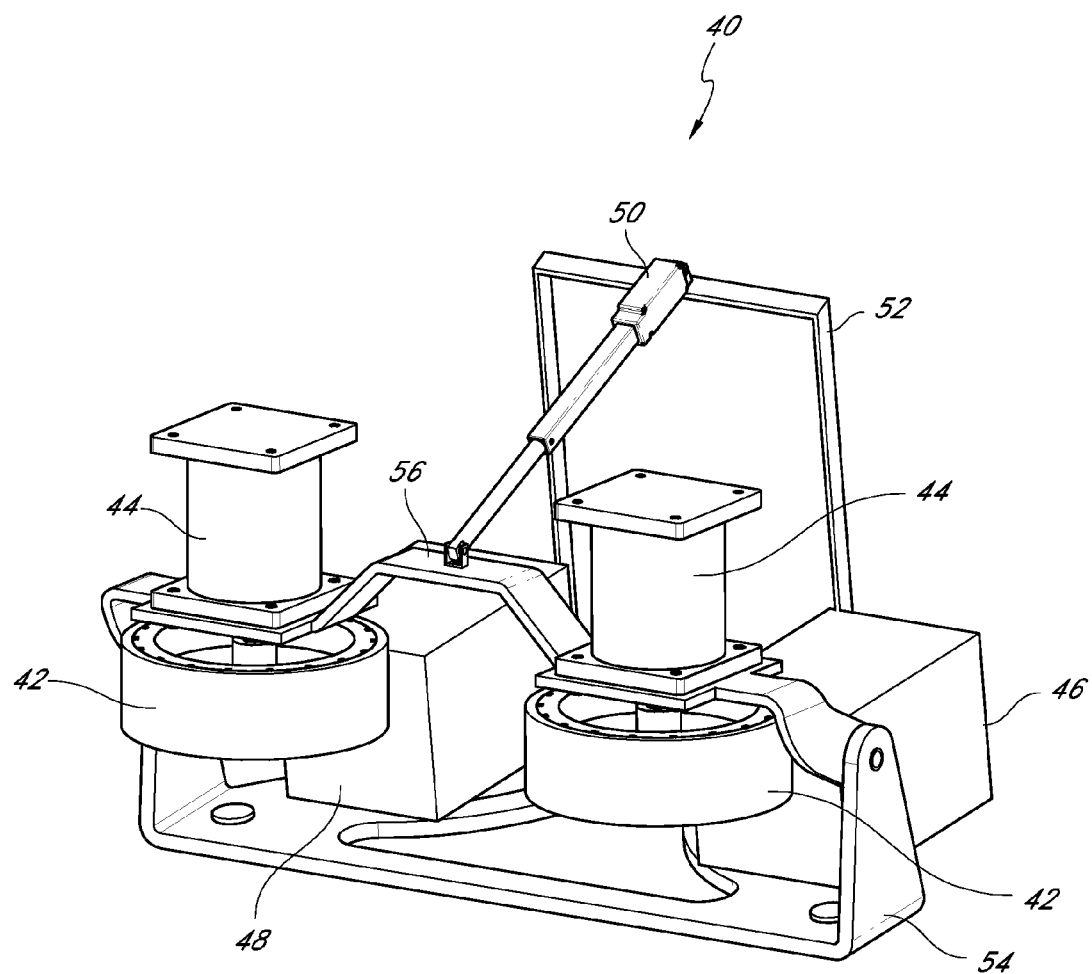
FIG. 3 shows some of the internal components of the ball throwing machine including portions of a ball delivery device.

Turning now to FIG. 3, an embodiment of a ball delivery device 40 is shown. A ball delivery device 40 can include any number of various components. The ball delivery device 40 can be used to impart motion to a ball. In some embodiments, the ball delivery device 40 can be used to control the trajectory of the ball, including the speed and angle at which the ball leaves the ball throwing machine 10. The ball delivery device 40 can perform these functions in various different manners including those described below. It is to be understood that the ball delivery device 40 also encompasses various other systems and methods of performing the above functions, as well as, other, additional and/or alternative functions.

As illustrated, the ball delivery device 40 includes one or more wheels or balls 42 which are used to impart speed, spin, and/or other features of trajectory to a ball. The ball delivery device 40 can also include one or more motors 44 which are connected to the wheels 42 to thereby deliver speed and direction to the wheels 42. The ball delivery device 40 can also include a control unit 46 and a power source 48, such as batteries. The control unit 46 can include various features that can be used to control the ball delivery device 40. For example, the control unit 46 can include electronic circuitry, a processor, and memory having program instructions stored thereon for controlling the various electrical features of the ball delivery device 40, such as the motorized wheels 18 and actuators (described below). Further, the control unit 46 can include a wireless network interface card (NIC) and antenna or wired NIC for communicating with a controller device that sends commands to the ball throwing machine 10, as described below with respect to FIG. 6.

The ball delivery device 40 may also include one or more actuators 50. The actuator 50 can be used to control an angle of the ball delivery device, including the wheels 42. The ball delivery device 40 can include a frame having one or more brackets 52, 54. The brackets 52, 54 can be positioned in fixed relationship with one another. As shown, the actuator 50 is connected to at one end to bracket 52 and at an opposite end to bracket 56. The bracket 56 can be attached to the wheels and in some embodiments, the motors 44. The bracket 56 can also be hingedly attached to bracket 54. The actuator 50 can move to increase or decrease the length of the actuator.

In the illustrated position of FIG. 3, the longitudinal axis of each wheel 42, about which the wheel rotates, is generally vertical. Moving the actuator 50 can change this position and orientation of the axis and wheel 42 as changing the length of the actuator 50 can change the angle or positional relationship between the bracket 56 and the frame, including brackets 52 and 54. When the actuator 50 is lengthened, the distance between the bracket 52 and parts of the bracket 56 is increased. When the actuator 50 is shortened, parts of the bracket 56 are moved closer to the bracket 52. This can result in the axis moving either upward or downward towards a horizontal orientation. It will be understood that changing the angle of the wheels 42 can change the trajectory of the ball when it is ejected.

Moving now to FIGS. 4 and 5, another feature of the ball delivery device 40 will be described. The ball delivery device 40 can also include features to change the side-to-side trajectory of the ball. As can be seen, an actuator 50 can be located on the bottom of the ball throwing machine 10. Such an actuator can be located either internally or externally of the outer housing 12. A bracket 58 can be connected to the bracket 54 through a turntable 60. Such a connection can allow the bracket 54 to move with respect to the bracket 58. The actuator 50 can be connected to both brackets 54, 58 such that movement of the actuator 50 can change the positional relationship of portions of the bracket 54 with the bracket 58.

Figure 4:
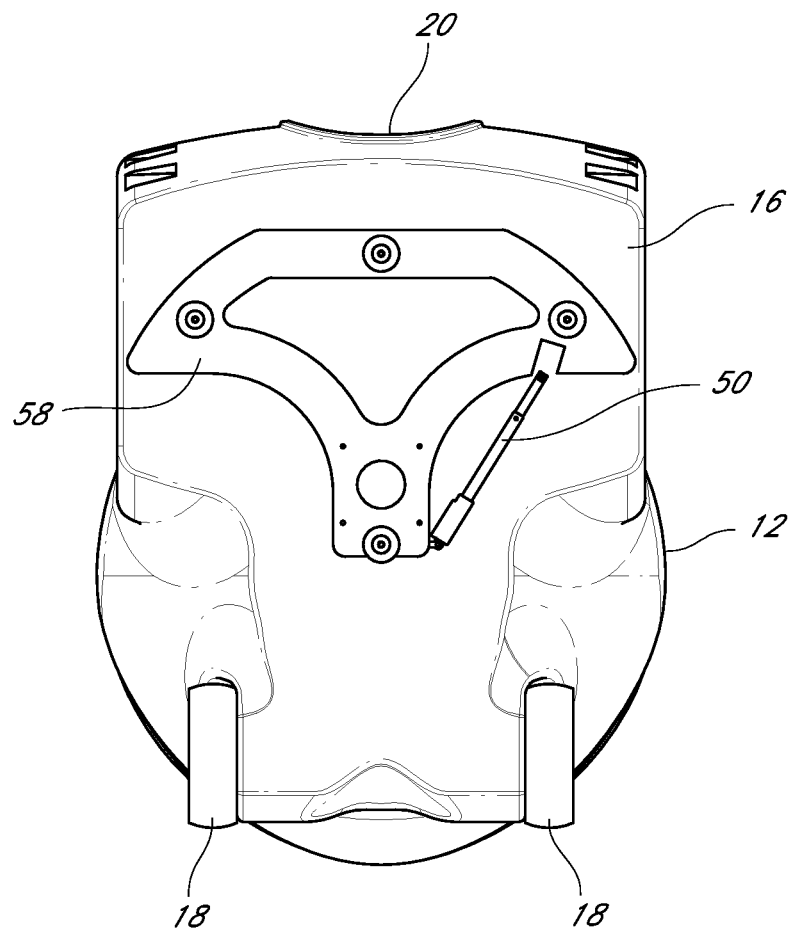
FIG. 4 illustrates the bottom of the ball throwing machine.
Figure 5:
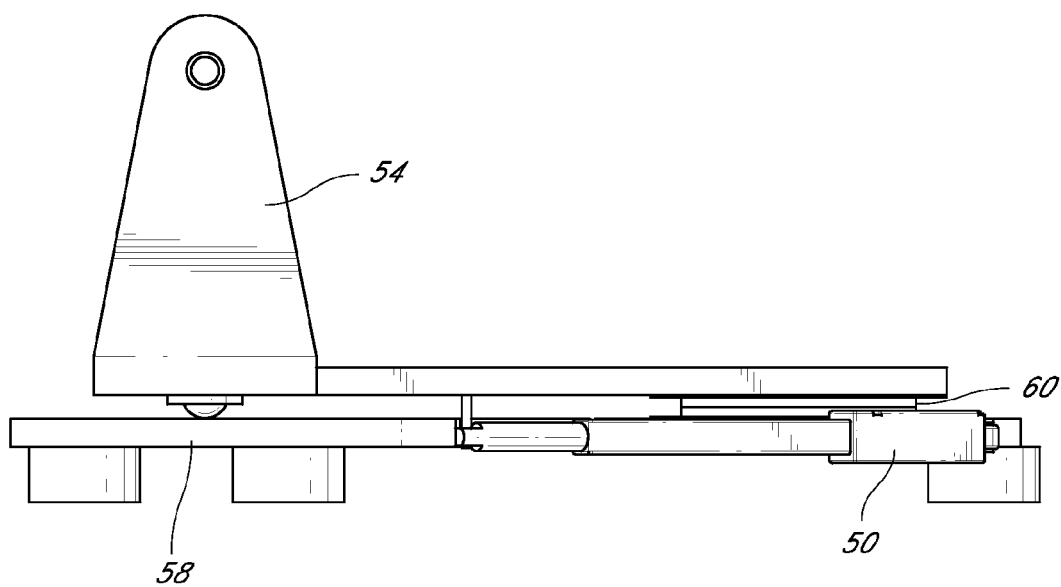
FIG. 5 shows portions of a ball delivery device.

Moving the actuator 50 illustrated in FIGS. 4 and 5 can change the relationship of a portion of the ball delivery device 40 with the opening 20. Thus, the ball delivery device can pitch the ball out the opening within a range of angles from the straight on position. For example, the ball delivery device can pitch the ball within ±10% or ±20% (or some other angle) of the straight-on position.

It will be understood that the ball delivery device 40 can function in many different ways, including ways different from those described herein. For example, rather than including an actuator, the ball delivery device 40 can be moved or positioned with one or more stepper motors connected directly between two rotating brackets. Further, although described as being primarily used for pitching soccer balls, the ball delivery device 40 can also be adapted to pitch other types of balls, such as baseballs, softballs, tennis balls, racquet balls, squash balls, cricket balls, lacrosse balls, volleyballs, and the like.

III. Example Training and Computing Environments

Figure 6:
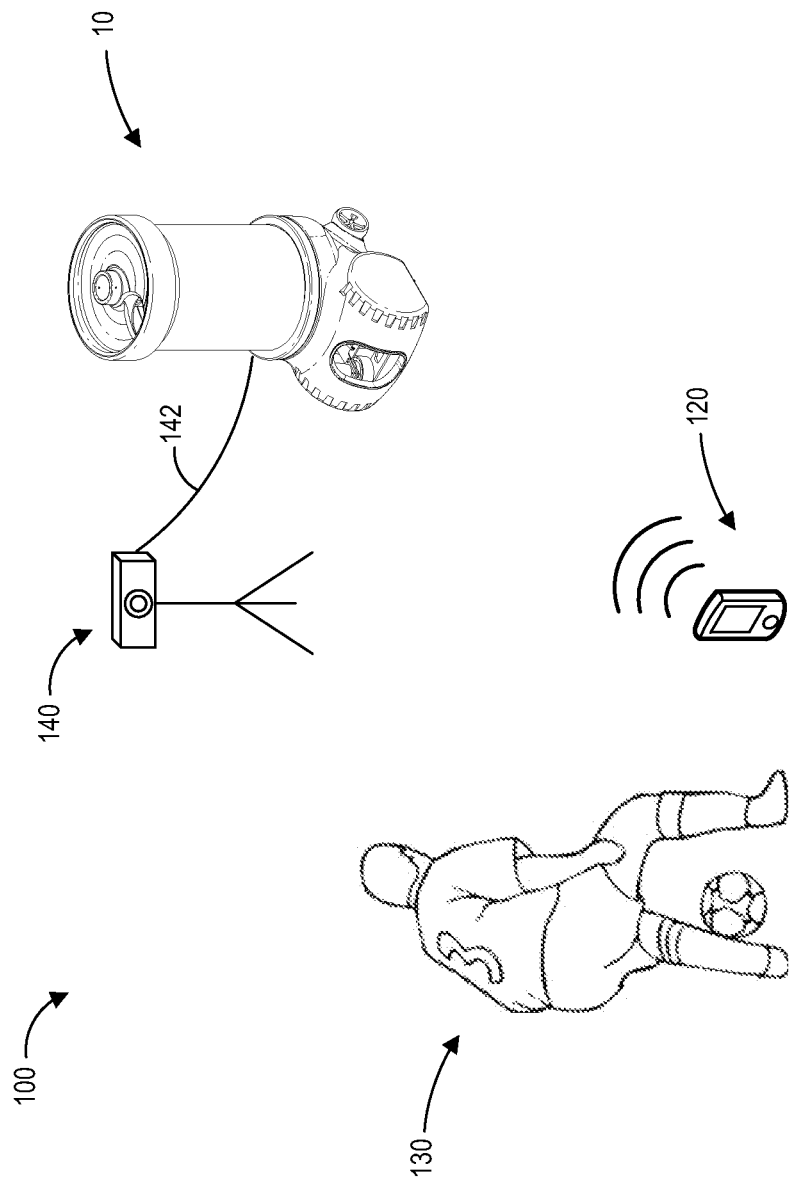
FIG. 6 illustrates an example training scenario using the ball throwing machine in conjunction with a controller.

FIG. 6 illustrates an example training scenario 100 for using the ball throwing machine 10 in conjunction with a controller 120. In the training scenario 100, a player 130 is training trapping or other ball control skills with the ball throwing machine 10. The player 130 may be any age or gender, and the ball throwing machine 10 can include settings that are appropriate for children, youth, and adults.

A controller 120 is also shown and is in wireless communication with the ball throwing machine 10. The controller 120 can be a computing device of the player 130 (or the player's coach or parent), and may be, for example, a smart phone, tablet, laptop, personal digital assistant (PDA), or other wireless handheld device, or even a desktop in some embodiments. The controller 120 can communicate wirelessly with a wireless module in the ball throwing machine 10 (e.g., in the control unit 46). Alternatively, the controller 120 can be coupled with the ball throwing machine 10 using a cable or a docking station installed in the ball throwing machine 10.

The controller 120 can include functionality for controlling the training programs that run on the ball throwing machine 10. For example, the controller 120 can include functionality for a user thereof, such as the player 130, coach, or a parent, to select training programs to be communicated to the ball throwing machine 10. Each training program can include a set of drills, commands, or instructions to be executed by the ball throwing machine 10, such as how many balls to throw in a given period of time, how fast, and with what trajectory. The training programs can be selected and customized by the player 130, a coach, or a parent.

An optional camera 140 is shown in communication with the ball throwing machine 10 via a cable 142. The camera 140 can take pictures or video of the player 130 during training sessions. The camera 140 can transmit the pictures and/or video to the ball throwing machine 10 over the cable 142 (or a wireless link). In turn, the ball throwing machine 10 can provide the pictures and/or video to the controller 120 wirelessly. Alternatively, the camera 140 can communicate directly with the controller 120, for example, by wirelessly sending pictures and video to the controller 120. Further, in some embodiments, images or video can be taken of the player 130 using a camera in the controller 120 or a built-in camera in the ball throwing machine 10 (not shown) instead of or in addition to the camera 140. In addition, in some embodiments, the camera 140 can communicate with player recognition software running in a processor or controller of the ball throwing machine 10. This player recognition software can locate a player and cause the ball throwing machine 10 to automatically throw a ball to the player. The player recognition software can include facial recognition software but may also detect a player from features of the player other than the face.

Advantageously, in some embodiments, the player 130 can use the controller 120 to submit pictures, video, or other player training data to a remote web site or network application (described below with respect to FIG. 7). The web site or network application may provide functionality for a coach to evaluate the player training data and provide feedback, including customized training programs that can be executed by the ball throwing machine 10.

Figure 7:
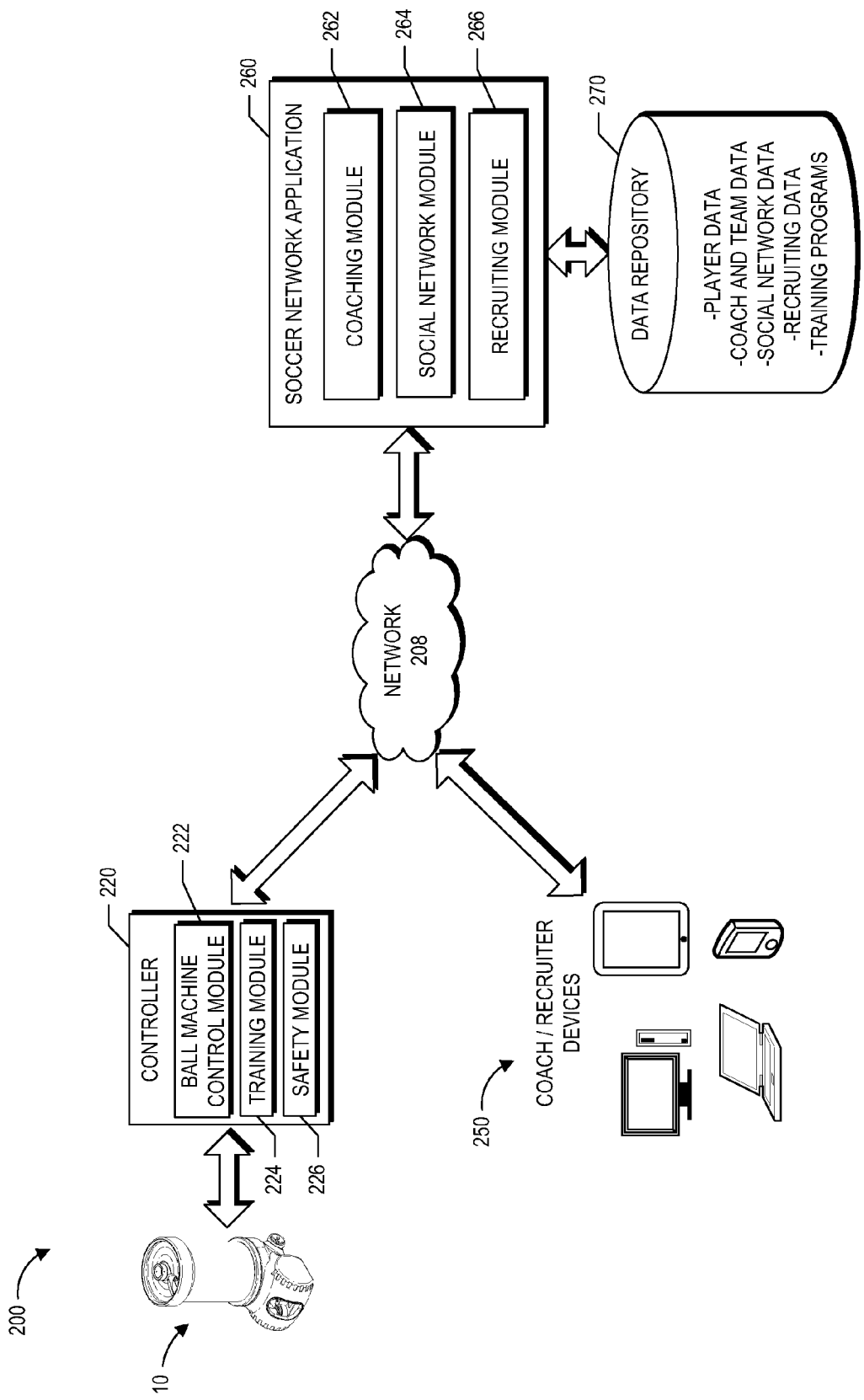
FIG. 7 illustrates an embodiment of a computing environment for facilitating communications between the controller of FIG. 6 and a soccer network application.

FIG. 7 illustrates an embodiment of a computing environment 200 for facilitating communications between the ball throwing machine 10, a controller 220, and a soccer network application 260. Advantageously, in certain embodiments, the computing environment 200 enables players to track player training data regarding training sessions with the ball throwing machine 10 and provide the player training data to a coach via the soccer network application 260. The coach can use the soccer network application 260 to provide feedback to the player, including customized training programs, based on the players' progress with the ball throwing machine 10.

By way of overview, the ball throwing machine 10 communicates with the controller 220, for example, wirelessly using WiFi (IEEE 802.11x), Bluetooth, Zigbee, or any other standard protocol(s). The controller 220 is a more detailed example of the controller 120 of FIG. 6 and can have all the features of the controller 120 described above. The controller 220 can communicate with the soccer network application 260 over a network 208, which may be a LAN, a WAN, the Internet, or combinations of the same. Devices 250 operated by coaches and/or recruiters may also communicate with the soccer network application 260 (or directly with the controller 220 or machine 10) over the network 208.

In the depicted embodiment, the controller 220 includes a ball machine control module 222, a training module 224, and a safety module 226. Each of these components can be implemented with hardware and/or software. In one embodiment, the modules 222, 224, 226 are part of a controller application installed on the controller 220. The controller application may be obtained for installation on the controller 220 from an application store (such as the iTunes™ application store or Android™ Market application store), via computer-readable media (such as a USB key or DVD), or the like. In some embodiments, the controller 220 is sold or otherwise provided together with the ball throwing machine 10 with the controller application preinstalled. Other functionality may also be provided with the controller 220 in some implementations.

The ball machine control module 222 of the controller 220 can provide functionality for a user (such as a player, coach, or parent etc.) to control the ball machine 10. For instance, the ball machine control module 222 can output a user interface that provides options for a user to select different types of training programs or individual ball throwing characteristics to be implemented by the ball throwing machine 10. This user interface can be implemented on a touch screen display of the controller 220 in some devices, although other types of controller 220 displays may also be used. In response to receiving user input regarding a desired training program or throwing pattern, the ball machine control module 222 can send instructions or commands to the ball throwing machine 10. A processor or other circuitry in the ball throwing machine 10 (such as the control unit 46) can receive and execute these instructions. The ball machine control module 222 can therefore enable a user to control any functions of the ball throwing machine 10, including but not limited to ball velocity, ball delivery (e.g., air, ground, line, lob, or bounce), ball trajectory (e.g., angled, curved, or straight), ball oscillation (e.g., side-to-side or middle-to-side), ball throwing frequency (e.g., every user-specified number of seconds), and the like.

The training module 224 can provide functionality for a user to record data regarding the player's usage of the ball throwing machine 10. For example, the training module 224 may provide a training user interface that enables a user to record this player training data (see, e.g., FIG. 13). This player training data can include a log of the commands sent to the machine 10, the commands executed by the machine 10, the user's success with traps or goals or other ball-control drills, video data, and the like. In one example implementation, the training module 224 provides user interface controls (such as touch-screen controls) that enable a user to input whether a trap is successful. The training module 224 may also include voice recognition functionality, using any commercially-available voice recognition software. A user can therefore dictate verbal training results to the training module 224, such as "successful trap" or "missed trap," or simply just "success" or "miss," or the like. The training module 224 can interpret the voice commands and record the interpretation (e.g., a success or miss) in the player training data. The training module 224 can supply the player training data to the soccer network application 260 (described below) over the network 208.

The safety module 226 can provide a user interface that enables users to manage safe use of the ball throwing machine 10. For instance, the safety module 226 can provide parental controls or the like that enable a parent, coach, or other responsible person to manage access to the ball throwing machine 10 or features thereof. It can be desirable to have such features to prevent accidents that can occur, for example, from setting the ball velocity or throwing frequency too high for younger players. These parental controls can include an authentication mechanism (such as a username/password or other credential) for enabling access to the machine 10, control over ball-throwing parameters such as velocity, and an idle or timeout feature that can shut down the controller 220 and/or ball throwing machine 10 after a timeout period of inactivity (such as 30 seconds, a minute, or some other time). Any of these safety features can also be implemented directly in the electronics of the ball throwing machine 10, rather than in the controller 220.

The soccer network application 260 can store player training data received from the training module 224 in a data repository 270. The data repository 270 can include any form of physical computer data storage, as well as logical computer storage. For instance, the data repository 270 can include one or more databases, associated physical storage media, and the like. The soccer network application 260 can include hardware and/or software for providing players (via the controllers 220 or other devices), coaches, and recruiters with access to the player training data, among optionally other data and features. The soccer network application 260 includes, in the depicted embodiment, a coaching module 262, a social network module 264, and a recruiting module 266. These modules represent at least some of the functionality that the soccer network application 260 may provide to players, coaches, recruiters, and others.

Each of the modules 262, 264, 266 can provide user interfaces for users to access features of the modules 262, 264, 266. For instance, the coaching module 262 can provide one or more user interfaces that enable a coach to access and analyze player training data for a plurality of players associated with that coach. If the player training data includes video, for instance, the coaching module 262 can provide functionality for the coach to view videos of players. The coaching module 262 can also provide functionality through one or more user interfaces for a coach to provide feedback to players. This feedback may be in the form of textual feedback, video feedback, or training program feedback. A coach may, for instance, respond to the uploading of a player's training data with comments on the player's form and suggest adjustments to the player's training program. Beneficially, in some embodiments, the coaching module 262 also enables a coach to select or create a training program to provide to a player as homework or the like. The coaching module 262 may provide a user interface for creating a custom training program for a specific player (see FIG. 16).

Moreover, the coaching module 262 can enable a coach to better leverage his or her time when training players. In the past, a coach has typically spent a few hours per week with an entire team of players, and the coach's ability to provide individual attention to those players has been limited. Further, a coach is typically not present when a player is practicing at home or with friends. However, with the soccer network application 260, a coach can evaluate player training data for several players and provide individualized feedback and training program recommendations to those players, without leaving his or her home. Thus, the soccer network application 260 can enable coaches to focus more individual attention on the development of players' ball control and trapping skills.

The social networking module 264 can provide functionality for different players, coaches, and the like to interact together in an online soccer community. For example, the social networking module 264 can provide user interfaces for creating player or coach pages, discussing soccer training with teammates and friends, uploading pictures and video, linking to web sites regarding soccer or other topics, and other features that may be found in any social network. Generally, the social network provided by the social networking module 264 can enable users to keep track of each other's progress in training with the ball throwing machine 10 and encourage each other in their progress. The social network module 264 may also provide an event user interface that enables users to coordinate events, such as impromptu soccer games, among other features.

The recruiting module 266 can provide a recruiting user interface that enables recruiters to examiner player data and/or for players or coaches to upload player data to recruiters. Some examples of recruiters that can use such features include high school recruiters, college recruiters, and professional recruiters. In one embodiment, the recruiting user interface enables recruiters to view player training data obtained with respect to the ball throwing machine 10. Advantageously, in certain embodiments, player training data obtained in conjunction with the ball throwing machine 10 can provide a standardized approach to reviewing player performance. Other player data may also be stored in the data repository 270 and made available to recruiters via the recruiting user interfaces, such as in-game data, coach reviews, scout reports, and the like.

It should be noted that the soccer network application 260 can be implemented as one or more physical servers. These servers may be geographically dispersed or co-located. In addition, in some embodiments, the soccer network application 260 is implemented as a cloud-computing platform. For example, the soccer network application 260 can be implemented as one of a plurality of virtual machines executing on a hypervisor, which can be a thin layer of software executing on a physical machine. Accordingly, the modules 262, 264, 266 of the soccer network application 260 can be implemented in hardware and/or software.

Further, it should be noted that although the features of FIGS. 6 and 7 as well as the features in subsequent FIGURES can be implemented in conjunction with the ball throwing machine 10, other ball throwing machines than the one explicitly described may also be used. For example, a throwing machine designed for a different sport can be controlled by the controller 120 or 220, or a different soccer-ball throwing machine can be used with the controller 120 or 220.

IV. Example Training Processes

Figure 8:
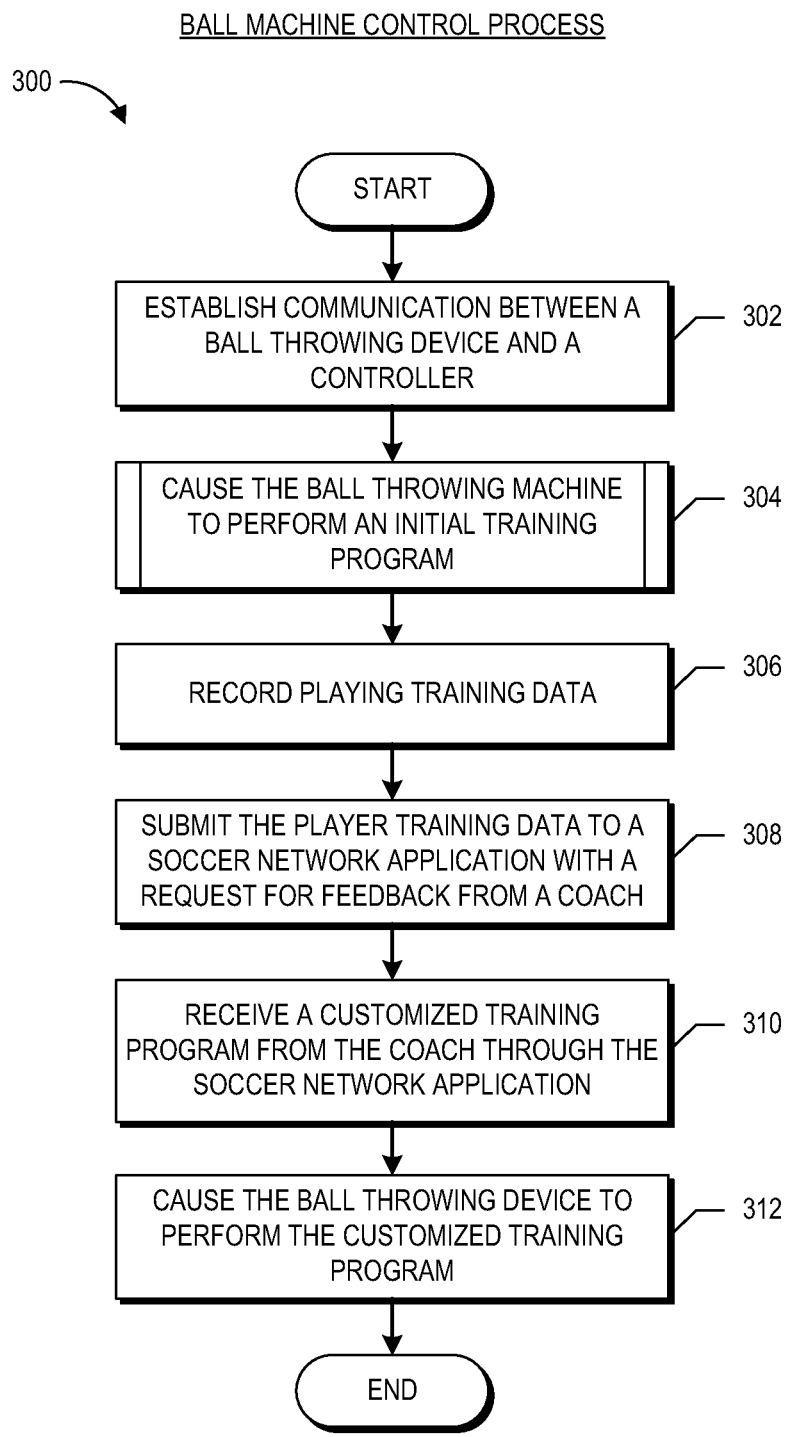
FIG. 8 illustrates an embodiment of a ball machine control process that may be implemented by the controller of FIG. 6.

FIG. 8 illustrates an embodiment of a ball machine control process 300 that may be implemented by the controller 220 (or 120). The ball machine control process 300 can enable a player to run customized training programs on a ball throwing machine, such as the ball throwing machine 10. Advantageously, these customized training programs can be designed by a remote coach who creates or selects the programs based on the player's progress with the ball throwing machine.

The process 300 begins at block 302, where the ball machine control module 222 of the controller 220 establishes communication with a ball throwing device. The ball machine control module 222 can establish communication in one embodiment according to a wireless or other network protocol. At block 304, the ball machine control module 222 causes the ball throwing machine to perform an initial training program. The performance of this initial training program is described in more detail below with respect to FIG. 9. As an overview, however, the initial training program can include one or more drills, which may include user-defined ball throwing commands or stored ball-throwing commands (which may have been stored by the player or coach).

At block 306, the training module 224 of the controller 220 records playing training data. There are many ways that this training data may be recorded, and many possible forms that the training data may take. Player training data can be recorded by the training module 224 automatically in one embodiment. For example, the training module 224 can log the commands issued by the controller 220 to the ball throwing machine, or may log the commands actually executed by the machine. For instance, the machine can report to the controller 220 which commands executed successfully and which did not execute successfully. Successful execution of a command can mean, in one embodiment, that the ball throwing machine performed a throw. The amount of data that the training module 224 collects regarding issued or executed commands can vary as well. This data can include characteristics of a throw, such as the ball's velocity (or desired velocity), delivery (or desired delivery), trajectory (or desired trajectory), oscillation (or desired oscillation), and/or frequency (or desired frequency). Any subset of this information may be collected and stored by the training module 224 in computer storage. Alternatively, the training module 224 merely records that a throw command was issued or occurred. In yet another implementation, the training module 224 records the target area or target zone on the player's body that the throw is aimed at (see FIG. 12).

As described above, the training module 224 may provide a user interface or voice recognition that enables a user to record whether a trap was successful. The player training data may include this success/lack of success information in addition to, or instead of, the more detailed throw or ball characteristics described above. In some embodiments, the training module 224 obtains an electronic indication of whether a player successfully trapped a ball or at least came in contact with the ball. This electronic indication can come from one or more sensors embedded in or placed on a players' clothing. Sensors can be placed or embedded anywhere on or in a player's clothing or on a player's person. Some example areas where sensors may be placed include the chest area, legs, thighs, feet, on the player's head, or any other location on the player's clothing or body. The sensors can be pressure sensors, contact sensors, or any other form of sensor that can produce an electronic output responsive to contact with a ball. For example, a player's shoe may have sensors embedded in one or more surfaces of the shoe to track whether the ball came into contact with such surfaces. Further, in some implementations sensors may be placed in a goal net (and/or on the posts) to determine whether the player has shot a ball in the goal. The sensors may communicate wirelessly with the controller 220 and/or ball throwing machine to provide sensor data to the training module 224. The training module 224 can incorporate the raw sensor data or processed versions thereof into the player training data. Accordingly, the player training data can include automatic indications of whether a trap was successful, or at least whether the ball came into contact with a player. One or more sensors can also be embedded in any of the balls described herein to track trapping, shooting, and other soccer skills.

The player training data may also include video data as described above. Further, the training module 224 can record any subset of the training data described herein. At block 308, the training module 224 submits the player training data to the soccer network application 260 with a request for feedback from a coach. This request for feedback may be explicit or implicit. For instance, a player can access a feature of the training module 224 that enables submission of player training data to the soccer network application 260. The soccer network application 260 may in turn make this player training data available to a coach of the player, or to a pool of coaches from which one is assigned or who picks the player training data for analysis. In another example scenario, the player can explicitly request the feedback of a particular coach when submitting the player training data to the soccer network application 260.

At block 310, the training module 224 receives a customized training program from the coach through the soccer network application 260. The customized training program can have any characteristics of any of the training programs herein. In one embodiment, the customized training program received includes a set of commands that the ball machine control module 222 can transmit to the ball control machine. In another embodiment, the coach can provide textual, verbal, or video instructions to the player regarding how to customize the player's training. The coach may also provide both an actual training program (including drills or machine commands) and textual, verbal, and/or video feedback. It should be understood, however, that the coach may not actually provide machine-level commands to the controller 220 (although this can be done in some embodiments). Rather, the soccer network application 260 can provide one or more user interfaces that enable a coach to select or define a training program having one or more drills. In response to that selection or definition, the soccer network application 260 can generate the appropriate commands that can be executed on the ball throwing machine.

At block 312, the ball machine control module 222 causes the ball throwing device to perform the customized training program. Thus, the ball machine control process 300 can enable a player to receive individualized attention from a remote coach on ball trapping skills or other soccer skills.

Figure 9:
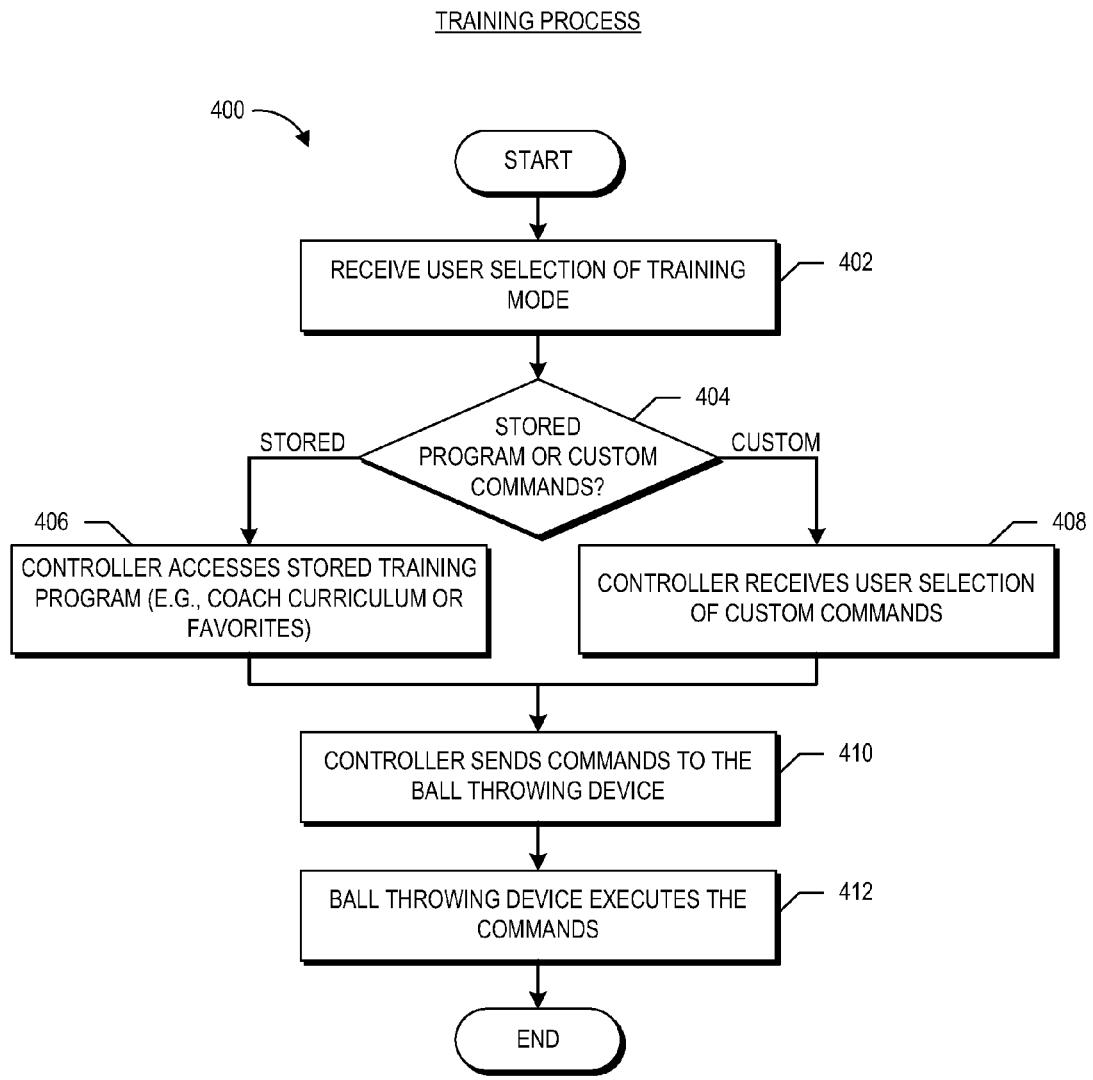
FIG. 9 illustrates an embodiment of a training process that may be implemented using the ball throwing machine and the controller of FIG. 6.

FIG. 9 illustrates an embodiment of a training process 400 that may be implemented using the ball throwing machine 10 and the controller 120 or 220. The training process 400 is a more detailed example implementation of the initial training program block 304 described above with respect to FIG. 8. The training process 400 may be implemented, for example, by the ball machine control module 222 of the controller 220.

At block 402, the ball machine control module 222 receives a user selection of training mode. A variety of training modes may be provided. These training modes may include, for example, the ability to access a stored program (or a program over a network), and the ability to perform custom training. This custom training can be a "free-play" type of training, where a user can define each ball's throwing characteristics as they are thrown. Although not shown, a random play mode is also available in some implementations, enabling a user to select a random series of throws having random characteristics (such as random velocity, angle, trajectory, and so forth). The custom training can also involve the user creating his or her own training program, which the user may subsequently store in memory of the controller 220 or ball throwing machine. The controller 220 may also provide functionality (such as a user interface or user interface control) for users to uploads custom training programs created with the controller 220 to the soccer network application 260, where other players or coaches can download the custom training programs. Further, the soccer network application 260 can provide user interface options to comment on and/or rate custom training programs, thereby enabling users to better decide which custom training programs to download.

At decision block 402, the ball machine control module 222 determines whether the user selection is for a stored program or custom commands. If the selection was for a stored program, the ball machine control module 222 accesses the stored program at block 406. The stored program may be a program created by the user and saved as a "favorite" program or the like. Alternatively, the stored program can be a training program provided by a coach. If the user selection was for a custom program, the ball machine control module 222 receives a user selection of custom commands at block 408. The ball machine control module 222 of the controller 220 sends the commands to the ball throwing device at block 410, which executes the commands at block 412.

Figure 10:
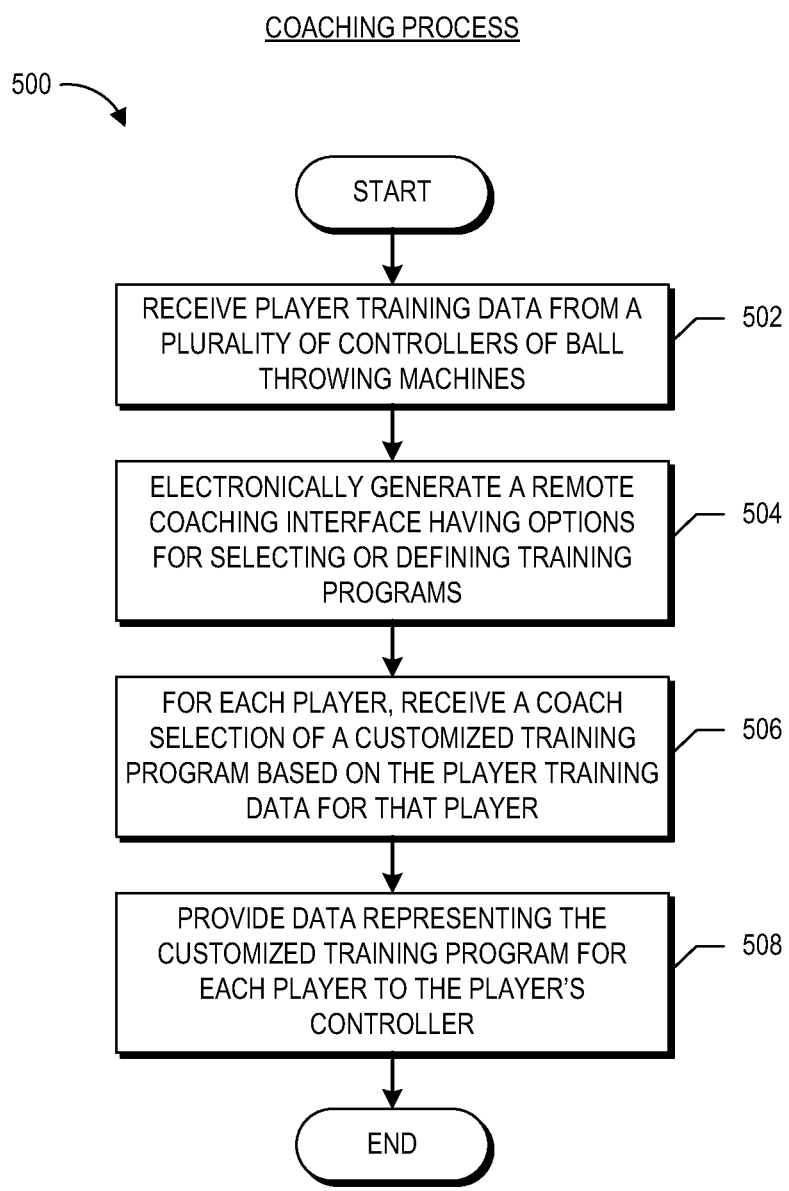
FIG. 10 illustrates an embodiment of a coaching process that may be implemented at least in part by the soccer network application of FIG. 7.

FIG. 10 illustrates an embodiment of a coaching process 500 that may be implemented at least in part by the soccer network application 260. In particular, the coaching process 500 can be implemented at least in part by the coaching module 262. The coaching process 500 can advantageously enable a coach to leverage his or her time to customize training for multiple players without having to be physically present with each of those players.

At block 502, the coaching module 262 receives player training data from a plurality of controllers of ball throwing machines, such as any of the controllers or machines described above. At block 504, the coaching module 262 electronically generates a remote coaching interface having options for selecting or defining training programs (see FIG. 16, described below). For each player, at block 506 the coaching module receives a coach selection of a customized training program based on the player training data for that player. In one embodiment, the coach selects or creates the training program. In another embodiment, the soccer network application 260 recommends the training program based on an automated analysis of the player training data. For example, the network application 260 can recommend a training program that is automatically customized to a player based on any of the following: previous drills performed by the player, age of the player, skill level of the player, a player's position, a past or recommended heart rate target for the player, combinations of the same, or the like. At block 508, the coaching module 262 provides data representing the customized training program for each player to the player's controller.

V. Example User Interfaces

Figure 14:
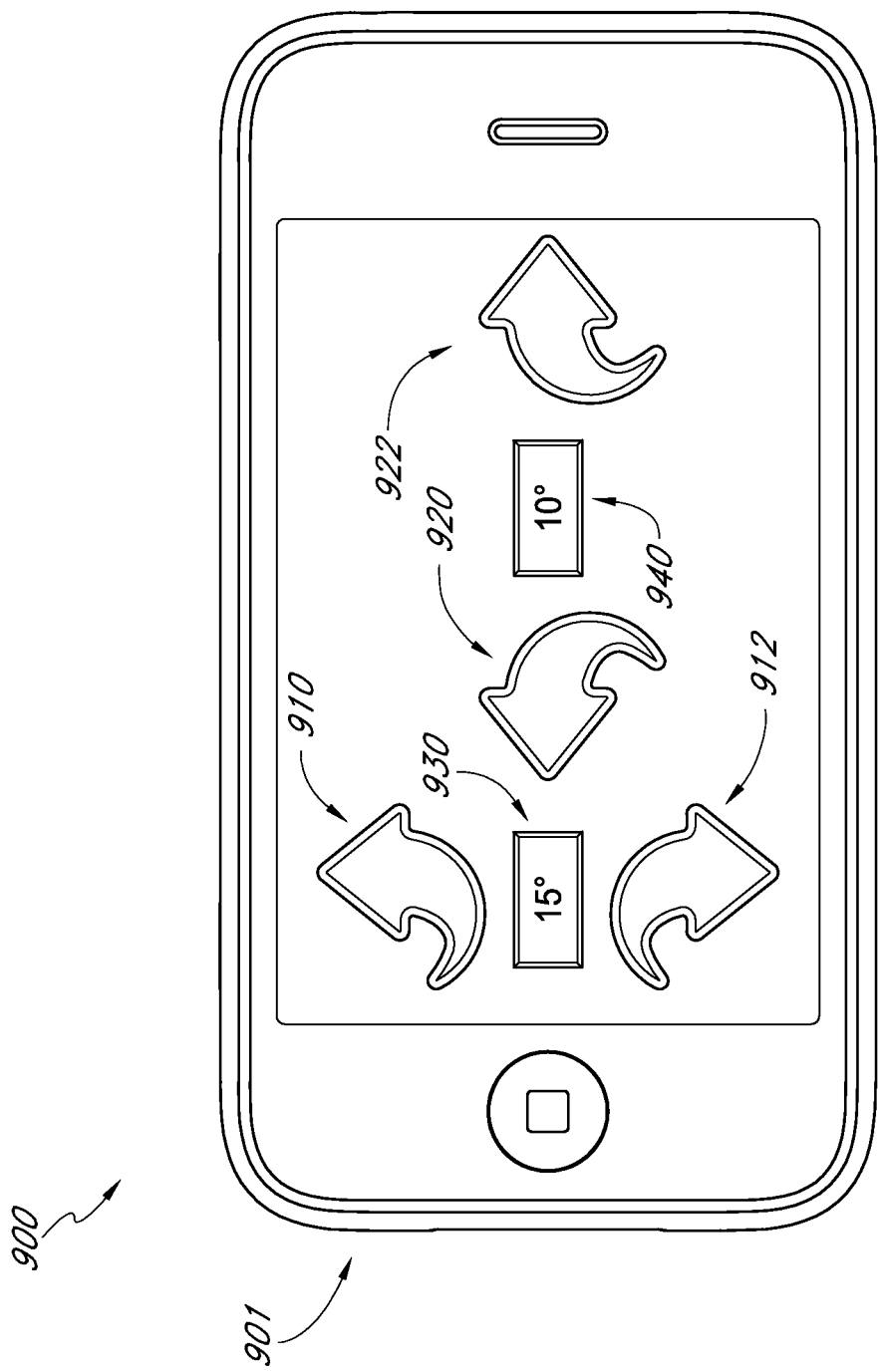
Figure 15:
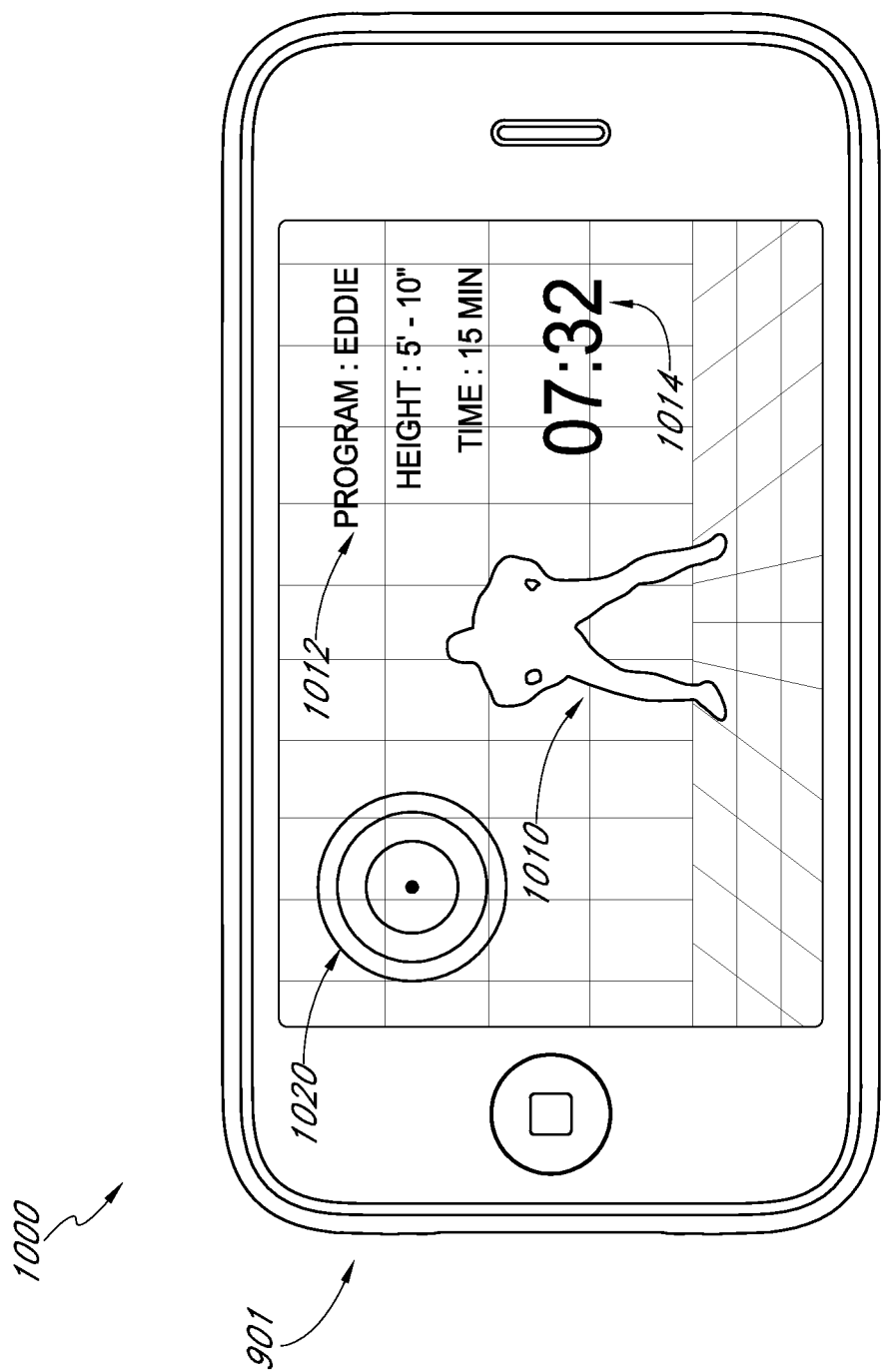
Figure 16:
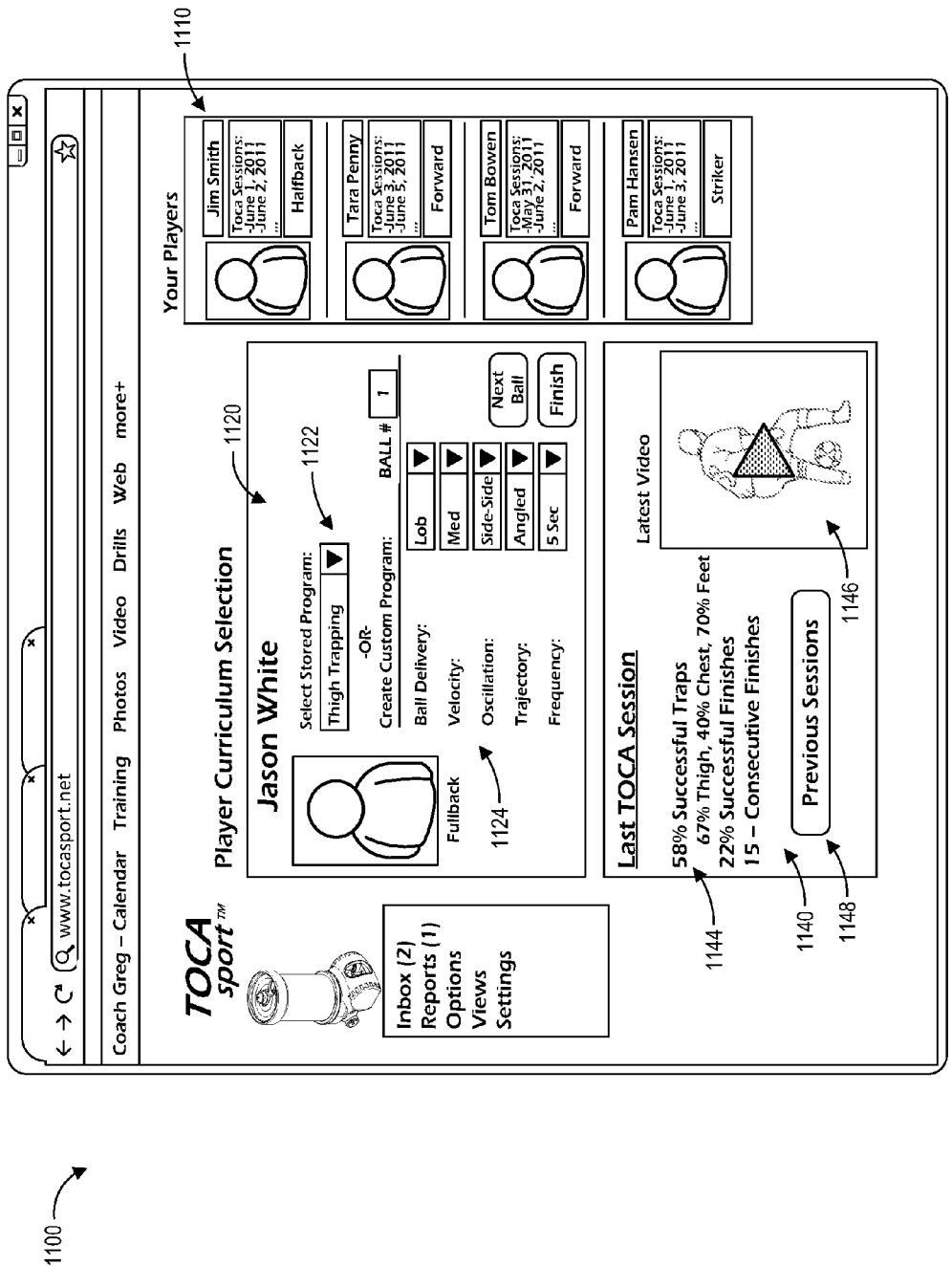
Figure 17:
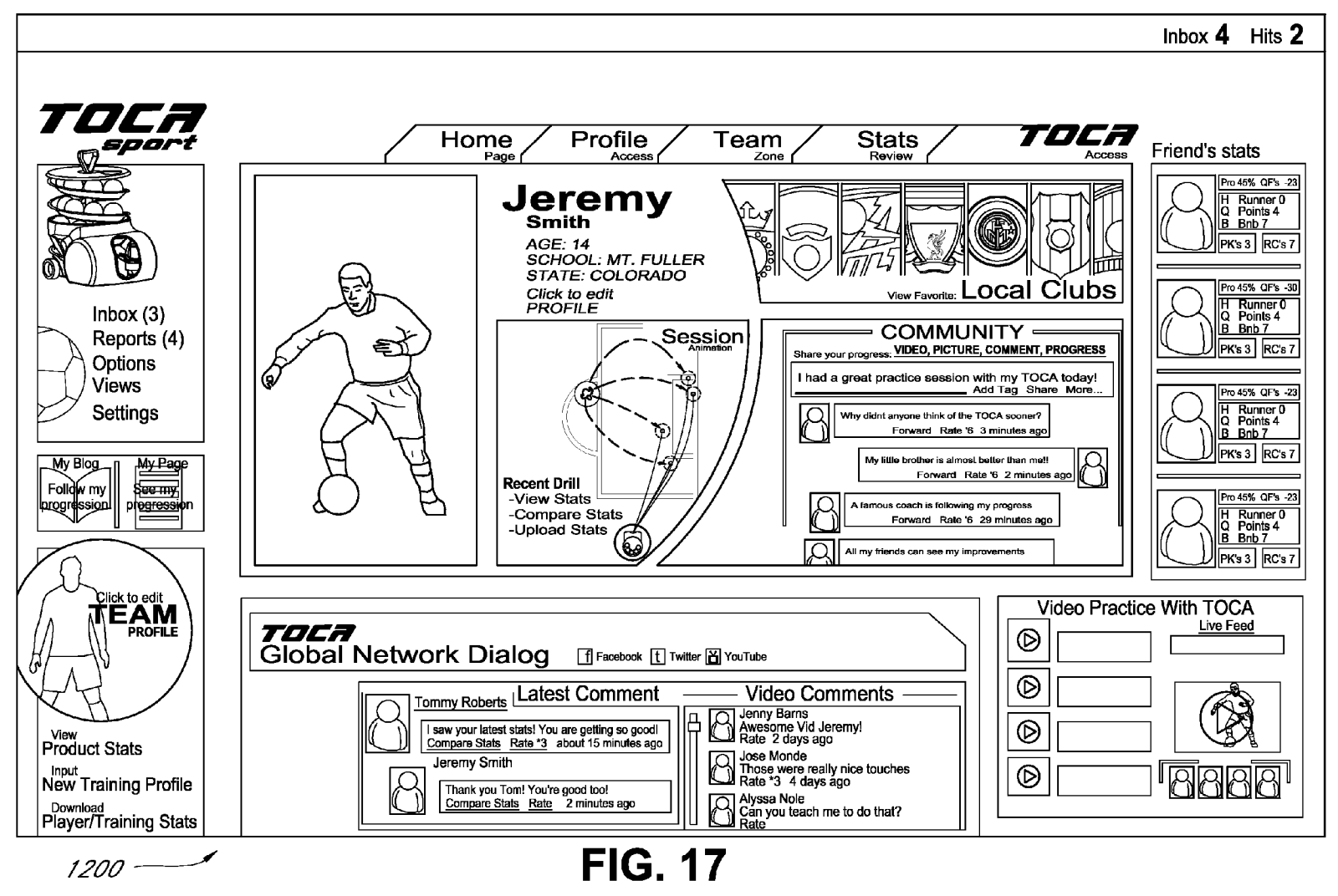

FIGS. 11 through 17 illustrate embodiments of controller user interfaces 600-1200 that may be generated by the controller 120 or 220. Each of these user interfaces 600-1200 may be generated by an application on a handheld computing device, such as a tablet or smartphone. In addition, the user interfaces 600-1200 may also be generated on another computing device, such as a laptop or desktop, as part of a web page rendered by a browser or by other software. In the example embodiments shown, FIGS. 11 through 15 illustrate example aspects of a controller application, while FIGS. 16 and 17 illustrate example aspects of a soccer network application.

Figure 11:
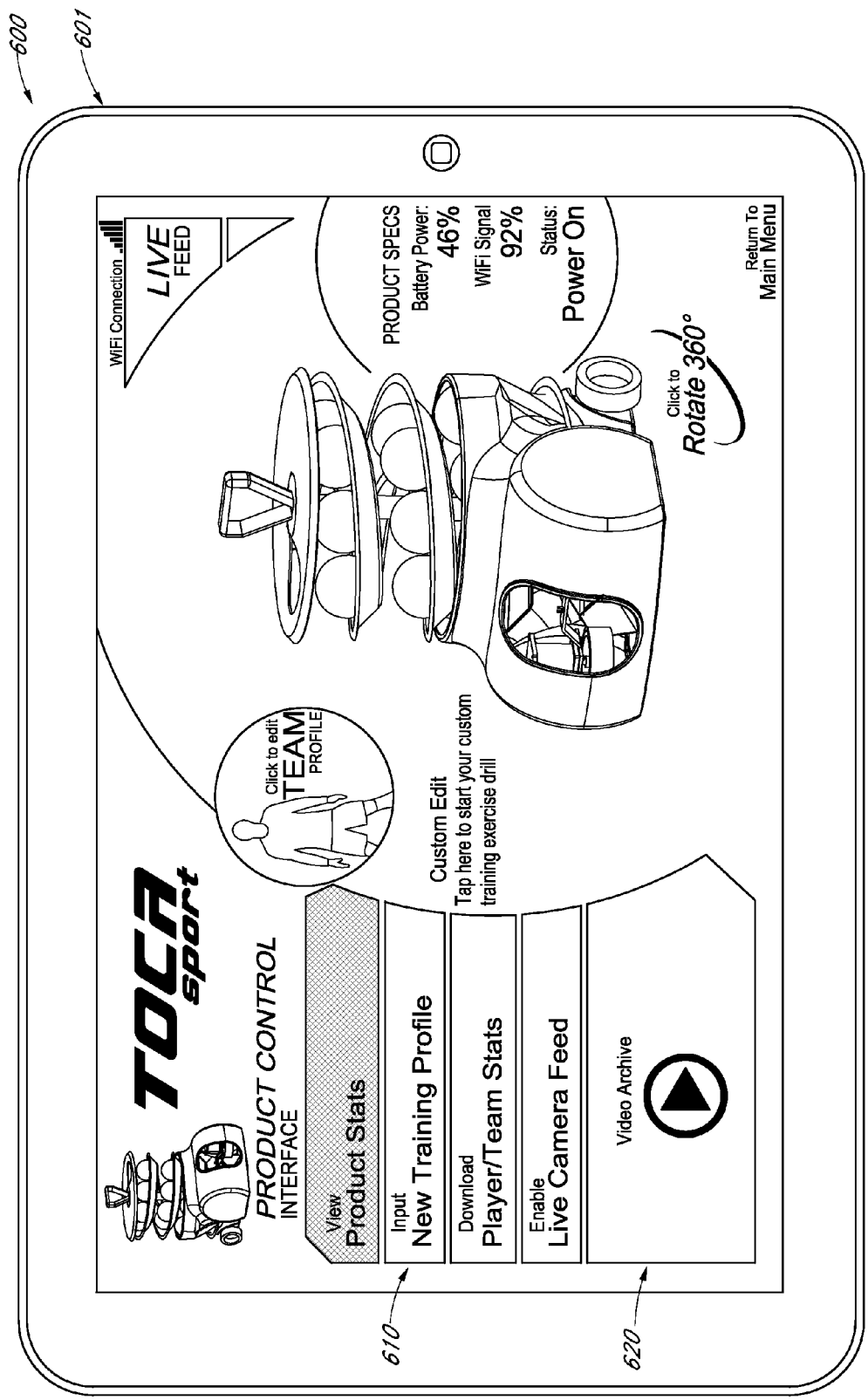
FIGS. 11 through 15 illustrate embodiments of controller user interfaces that may be generated by the controller of FIG. 6.

Referring specifically to FIG. 11, a controller user interface 600 is shown on a tablet device 601 for illustrative purposes, although other devices may be used to render the controller user interface 600. The controller user interface 600 includes controls 610 for accessing various options and may be generated by the ball machine control module 222. Example options shown include options to view product (ball machine) stats, create a new training profile to begin training, download player or team stats (from the soccer network application), and enabling a live camera feed. An addition control 620 is provided for viewing stored videos. These videos can be videos of the player, training videos on how to use the machine, or tutorials on how to improve soccer skills, to name a few.

Figure 12:
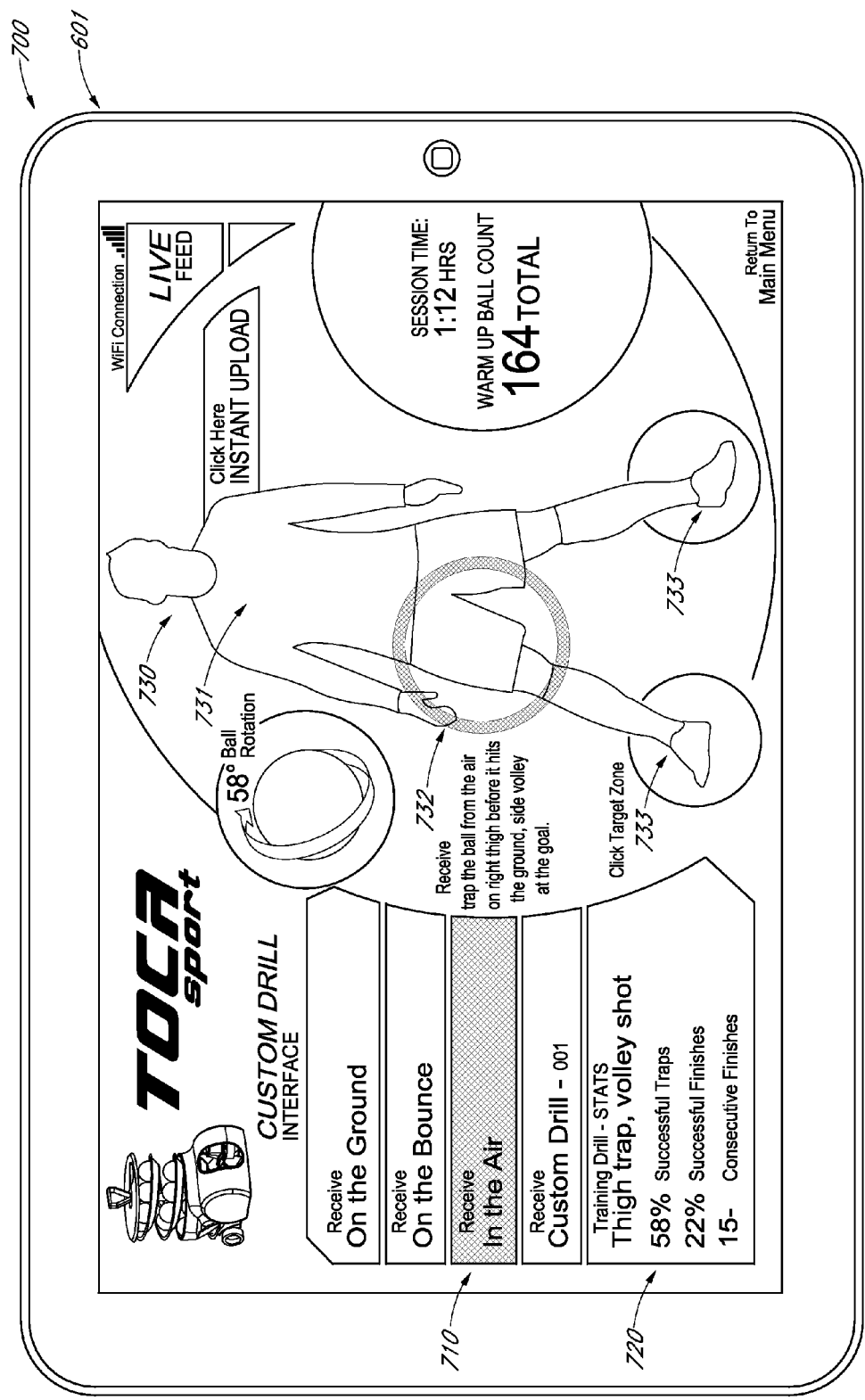

FIG. 12 illustrates another controller user interface 700, shown on the example tablet device 601 for illustrative purposes. The user interface 700 may be generated by the ball machine control module 222. The controller user interface 700 includes controls 710 for controlling various ball-delivery options, which enable a user to select whether to receive a ball on the ground, on the bounce, or in the air, or some other custom setting. Statistics 720 regarding the player's training drills are also shown, which indicate that for thigh traps, the player has made 58% successful traps, 22% successful finishes (e.g., shots on goal after trapping the ball), and 15 consecutive finishes. A graphic 730 illustrates a part of the player's body on which the ball should be trapped for a particular drill. In the embodiment shown, the graphic 730 highlights the player's thigh as the target zone 732 to which the ball will be thrown and trapped. In one embodiment, the user may select a target zone 731, 732, or 733 on the graphic 730 (using a finger, mouse, or the other input mechanism) to cause balls to be thrown to a different area of the player's body. For example, selection of a foot target zone 733 can cause the ball throwing machine to throw balls toward the player's feet.

More particularly, in one embodiment, selection of a foot target zone can cause the machine to throw a ball along the ground, or lob the ball toward the player's feet. The distance or approximate distance of the player to the machine may be input by a user into the controller 220 to thereby enable the machine to make such a lob. Similarly, selection of a thigh or chest target zone can cause the controller 220 can cause the machine to lob, bounce, or line drive the ball to a player's thigh or chest. The controller 220 may also provide functionality for other target zones to be selected, such as the head or the hands (for goalies). For example, the controller 220 can enable a player to select a spot away from the player where the player is to dive and catch the ball with his or her hands.

Figure 13:
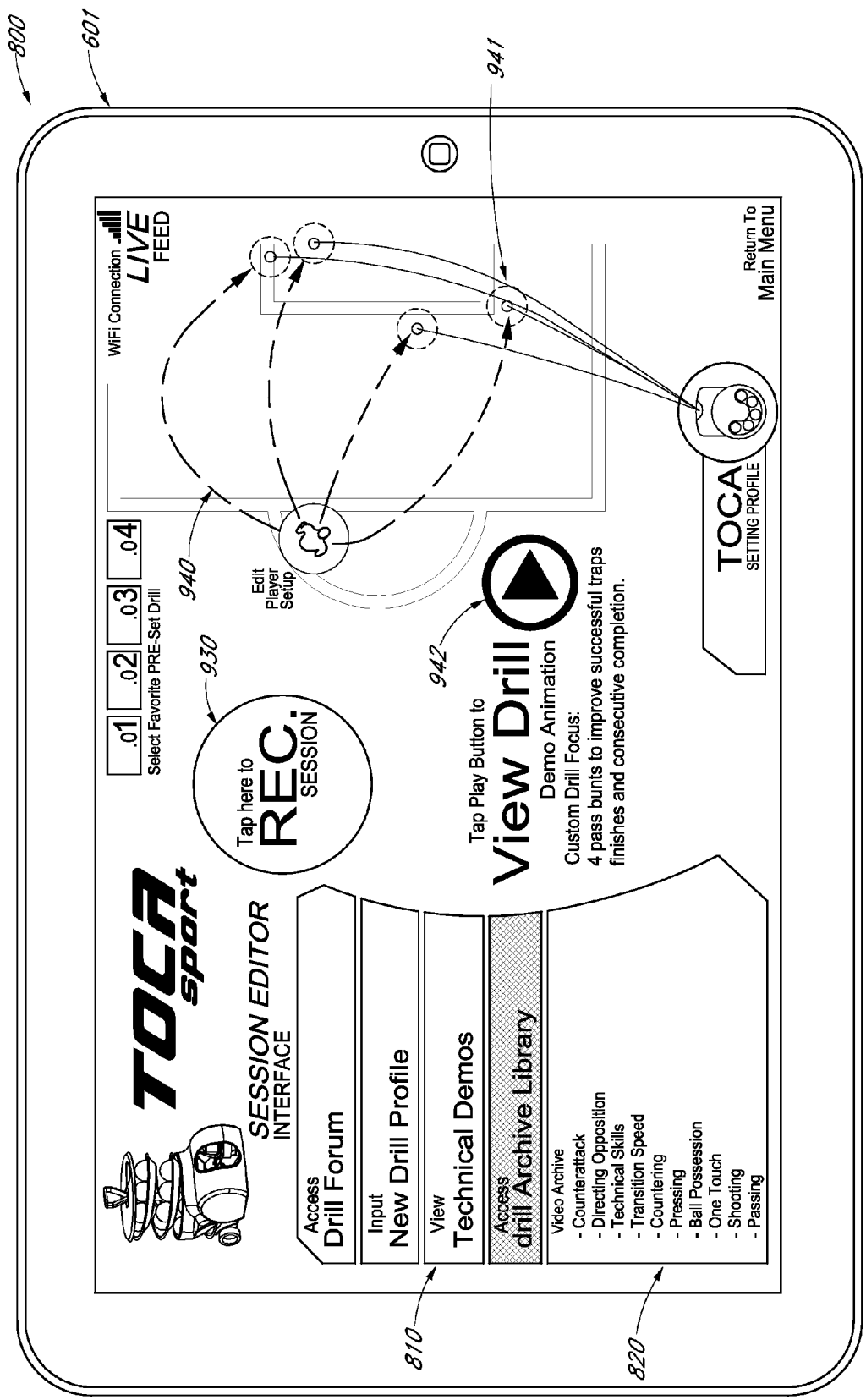

In FIG. 13, another controller user interface 800 is shown, also illustrated on the table device 601. The controller user interface 800 includes controls for a user to edit a training session by accessing a drill forum, inputting a new drill profile, viewing technical demos, or accessing a drill training library from which to select new drills. The drill forum can allow players to share drills and training ideas and can be implemented in a web site or other network application. Another control 820 is provided for accessing a video archive of drills. The user may record a training session using any of the recording techniques described above by selecting a record control 930. The record control 930 is an example of a control that may be provided by the training module 224 to record player training data. A specific selected drill 940 is also shown, which includes a series of projected ball trajectories 941. A demo control 942 is provided to enable a user to view a demo animation (or video) of how the drill 940 is to be performed.

FIGS. 14 and 15 illustrate additional example controller user interfaces 900, 1000 implemented in the context of a smartphone 901. It should be understood, however, that the user interfaces 900, 1000 may be implemented in other devices. Likewise, the other user interfaces described herein may be implemented on a smart phone. In FIG. 14, the user interface 900 includes arrow controls 910, 912, 920, 922 and angle controls 930, 940 to select a ball to be thrown in a specific direction. For example, selection of the up control 910 or down control 912 at an angle 930 of 15 degrees can cause the ball to be thrown up or down at an angle of 15 degrees from a horizontal plane (e.g., the ground). Similarly, selection of the left control 920 or right control 922 at an angle 940 of 10 degrees can cause the ball to be thrown left or right at an angle of 10 degrees from the vertical plane (e.g., perpendicular to the ground and intersecting the machine and the player). Multiple ones of the controls may be selected for any given throw. For instance, the up arrow 910 and the left arrow 920 may be selected simultaneously to cause a ball to be thrown to the upper left of the player at specified angles 930, 940.

In FIG. 15, the controller user interface 1000 includes a target zone 1020 that can be selected by a user, to which the ball machine will attempt to throw a ball. This target zone 1020 is shown relative to a graphic image of a player 1010. Thus, in the depicted embodiment, the target zone 1020 is to the right of the player's 1010 head, enabling the player to practice heading the ball. Statistics 1012 regarding the player, such as the player's name, height, and the time of the training program are shown as illustrative example statistics. Similarly, the time remaining 1014 in the program is also shown.

Referring to FIG. 16, an example coaching user interface 1100 is depicted as being in a web browser. A coach may access the coaching user interface via a web browser or other application software. The coaching user interface 1100 includes selectable controls 1110 that represent the coach's players, which include information such as their names, positions, their player training data, and so forth. Coach-selection of one of the player controls 1110 can cause a curriculum selection display 1120 to be produced on the user interface 1100 as well as player training data 1140 for a particular player. In an alternative embodiment, the user interface 1100 can enable the coach to create training programs without first selecting a player. The coach can save such training programs for subsequent selection by a player. Further, in some embodiments, the user interface 1100 may be used by a player to create a custom training program or modify another user's custom training program online. The player can then use the user interface 1100 to send the custom training program to a controller (220).

The example player training data 1140 shown includes data regarding the most recent session the player had with the ball throwing machine. This data includes trap completion data 1144 and video 1146. A button link 1148 to previous sessions is also provided. The curriculum selection display 1120 includes various controls 1122, 1124 that enable a coach to define a training program. These controls include a selection control 1122 for selecting a stored (e.g., previously-created) program and creation controls 1124 for creating a custom program. Some example parameters for creating a custom program are depicted with respect to the controls 1124, enabling a coach to define for each ball in a program its various characteristics (such as ball delivery type, velocity, oscillation, etc.). These characteristics are merely examples. In other embodiments, for instance, the coaching user interface 1100 may provide functionality for a coach to input the types of target zones each ball is directed to, such as the thigh, chest, foot, etc., in addition to or instead of the characteristics shown.

FIG. 17 illustrates an example social networking user interface 1200 that may be generated by the soccer network application 260. The social networking user interface 1200 includes profile information for a player, community features for discussing training progress, videos, and other related social networking features. For example, some potential features of the social networking user interface 1200 or other such user interfaces can include, among others, depicting of results of training or games, providing of tips and training advice, blogs, videos, player ratings, player rankings (including possibly highlight rankings for ranking impressive video-recorded training sessions), help request functionality for asking an expert or coach for help, comments from a professional, online webinars and training, contests, event organizations, recruiting tips, other recruiting features, general fitness training, and the like.

VI. Terminology

Many other variations than those described herein will be apparent from this disclosure. For example, depending on the embodiment, certain acts, events, or functions of any of the algorithms described herein can be performed in a different sequence, can be added, merged, or left out all together (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together. Although certain computer-implemented tasks are described as being performed by a particular entity, other embodiments are possible in which these tasks are performed by a different entity.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a personal organizer, a device controller, and a computational engine within an appliance, to name a few.

The steps of a method, process, or algorithm described in connection with the embodiments disclosed herein can be embodied directly in hardware, in a software module executed by a processor, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An exemplary storage medium can be coupled to the processor such that the processor can read information from, and write information to, the storage medium. In the alternative, the storage medium can be integral to the processor. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A soccer ball throwing device comprising:
   a hopper configured to hold a plurality of soccer balls;
   a ball delivery device configured to receive the soccer balls from the hopper, the ball delivery device comprising:
      one or more wheels configured to impart motion to one of the soccer balls, and
      a frame attached to the one or more wheels, wherein the frame is positionable to control a trajectory of the ball;
   a ball delivery control circuit configured to control the position of the frame and the speed of the one or more wheels; and
   a controller in communication with the ball delivery control circuit, the controller comprising one or more processors configured to at least:
      cause the soccer ball throwing device to perform an initial training program that comprises a set of one or more ball trapping drills, wherein the controller causes the soccer ball throwing device to pitch one or more of the soccer balls to a player during said one or more ball trapping drills, enabling the player to practice trapping the ball and thereby improve ball control skills;
      receive player training data, the player training data comprising information regarding training of the player performed during the initial training program, the player training data being received by one or more of the following:
         user input into a user interface, the user input indicating whether the player successfully trapped one or more of the balls; or
         user voice input received and electronically converted by voice recognition techniques into an indication of whether the player successfully trapped one or more of the balls;
      submit the player training data from the controller over a network to a soccer network application along with a request for feedback from a remote coach through the soccer network application; and
      in response to said submission of the training session data, receive a customized training program from the coach via the soccer network application, the customized training program comprising one or more second drills to be executed by the soccer ball throwing device.

2. The soccer ball throwing device of claim 1, wherein the angle of trajectory comprises an up and down angle and a side to side angle.

3. The soccer ball throwing device of claim 1, wherein the frame comprises a first bracket, a second bracket, and a mechanical actuator, wherein the mechanical actuator is configured to change a positionable relationship of the first bracket with respect to the second bracket.

4. The soccer ball throwing device of claim 1, further comprising a turntable configured to move the frame from side to side.

5. The soccer ball throwing device of claim 1, wherein the ball delivery device is configured to deliver soccer balls that are smaller than adult regulation size soccer balls to thereby enable more effective training of ball trapping skills.

6. A method of controlling a soccer ball throwing device, the method comprising:
   providing a soccer ball throwing device comprising:
      a hopper configured to hold a plurality of soccer balls,
      a ball delivery device configured to receive the soccer balls from the hopper, the ball delivery device comprising:
         one or more wheels configured to impart motion to one of the soccer balls, and
         a frame attached to the one or more wheels, wherein the frame is positionable to control a trajectory of the ball, and
      a ball delivery control circuit configured to control the position of the frame and the speed of the one or more wheels;
   communicating with the soccer ball throwing device via a controller comprising computer hardware;
   causing the soccer ball throwing device, with the controller, to perform an initial training program that comprises a set of one or more ball trapping drills, wherein the controller causes the soccer ball throwing device to pitch one or more balls to a player during said one or more ball trapping drills, enabling the player to practice trapping the ball and thereby improve ball control skills;
   receiving player training data, the player training data comprising information regarding training of the player performed during the initial training program, said receiving comprising receiving one or more of the following:
      user input into a user interface, the user input indicating whether the player successfully trapped one or more of the balls; or
      user voice input received and electronically converted by voice recognition techniques into an indication of whether the player successfully trapped one or more of the balls;
   submitting the player training data from the controller over a network to a soccer network application along with a request for feedback from a remote coach through the soccer network application; and in response to said submitting the training session data, receiving a customized training program from the coach via the soccer network application, the customized training program comprising one or more second drills to be executed by the soccer ball throwing device;

wherein said method is implemented by one or more physical processors.

7. The method of claim 6, wherein the ball delivery device is configured to deliver soccer balls that are smaller than adult regulation size soccer balls to thereby enable more effective training of ball trapping skills.

8. A method of controlling a soccer ball throwing device, the method comprising:

establishing communication between a soccer ball throwing device and a controller comprising computer hardware;

causing the soccer ball throwing device, with the controller, to perform an initial training program that comprises a set of one or more ball trapping drills, wherein the controller causes the soccer ball throwing device to pitch balls to a player during said one or more ball trapping drills, enabling the player to practice trapping the balls and thereby improve ball control skills;

receiving player training data, the player training data comprising information regarding training of the player performed during the initial training program, said receiving comprising receiving one or more of the following:

user input into a user interface, the user input indicating whether the player successfully trapped one or more of the balls; or user voice input received and electronically converted by voice recognition techniques into an indication of whether the player successfully trapped one or more of the balls;

submitting the player training data from the controller over a network to a soccer network application along with a request for feedback from a remote coach through the soccer network application; and in response to said submitting the training session data, receiving a customized training program from the coach via the soccer network application, the customized training program comprising one or more second drills to be executed by the soccer ball throwing device;

wherein said method is implemented by one or more physical processors.

9. The method of claim 8, wherein said causing the soccer ball throwing device to perform the initial training program comprises causing the soccer ball throwing device to pitch a ball to a specific trap location on the player.

10. The method of claim 9, further comprising providing functionality for the player to select the specific trap location from among one or more of the following: a foot, a thigh, a leg, the chest, a shoulder, and the head.

11. The method of claim 8, wherein said causing the soccer ball throwing device to perform the initial training program comprises causing the soccer ball throwing device to perform a specific type of throw.

12. The method of claim 11, wherein available type of throws comprises one or more of the following: throws on the ground, throws in the air, and throws that include a bounce.

13. The method of claim 8, wherein the player training data comprises video of the player captured during execution of the initial training program.

14. The method of claim 13, wherein the video is configured to be captured by one or more of the following: the controller, a camera installed on the soccer ball throwing device, and a separate camera in communication with the soccer ball throwing device.

15. A system for controlling a ball throwing device, the system comprising a ball machine control module configured to:

cause a soccer ball throwing device to perform an initial training program that comprises a set of one or more ball trapping drills, wherein the ball machine control module causes the soccer ball throwing device to pitch balls to a player during said one or more ball trapping drills, enabling the player to practice trapping the balls and thereby improve ball control skills; and a training module implemented in one or more processors, the training module configured to:

receive player training data, the player training data comprising information regarding training of the player performed during the initial training program, the player training data being received by one or more of the following:

user input into a user interface, the user input indicating whether the player successfully trapped one or more of the balls; or user voice input received and electronically converted by voice recognition techniques into an indication of whether the player successfully trapped one or more of the balls;

electronically submit the player training data over a network to a soccer network application along with a request for feedback from a remote coach through the soccer network application, and in response to said electronically submitting the training session data, receive a customized training program from the coach via the soccer network application, the customized training program comprising processor-executable instructions related to one or more second drills to be executed by the soccer ball throwing device;

wherein the ball machine control module is further configured to automatically cause the soccer ball throwing device to execute the one or more second drills responsive to the processor-executable instructions.

16. The system of claim 15, wherein the player training data comprises a log of pitches made by the soccer ball throwing device.

17. The system of claim 16, wherein the player training data comprises a log of successful traps made by the player during the initial training session.

18. The system of claim 17, wherein the log of successful traps is populated by input from the player.

19. The system of claim 17, wherein the log of successful traps comprises a trap completion percentage.

20. The system of claim 15, further comprising a safety module configured to enable a user to selectively control access to the soccer ball throwing device by the player.

21. The system of claim 20, wherein the safety module is further configured to enable the user to place a limit on ball throwing velocity.

22. The system of claim 20, wherein the safety module is further configured to enable the user to input a password to enable actuation of the ball throwing device.

23. The system of claim 20, wherein the safety module is configured to automatically disable the soccer ball throwing device after a period of idle time.

24. The system of claim 15, further comprising a favorites module configured to enable the player to save favorite training drills with respect to the soccer ball throwing device.

25. The system of claim 15, wherein the ball machine control module is further configured to provide functionality for user selection of a target zone of the player's body for delivery of a ball.

26. The system of claim 25, wherein the user selection of the target zone causes the soccer ball throwing device to throw the ball toward the selected target zone.

27. Non-transitory physical computer storage comprising instructions stored therein for implementing, in one or more processors, a system for controlling a ball throwing device, the system comprising:

a ball machine control module configured to cause a soccer ball throwing device to perform an initial training program that comprises a set of one or more ball trapping drills, wherein the ball machine control module causes the soccer ball throwing device to pitch balls to a player during said one or more ball trapping drills, enabling the player to practice trapping the balls and thereby improve ball control skills; and a training module configured to receive player training data, the player training data comprising information regarding training of the player performed during the initial training program, the player training data being received from one or more of the following:

user input into a user interface, the user input indicating whether the player successfully trapped one or more of the balls; or user voice input received and electronically converted by voice recognition techniques into an indication of whether the player successfully trapped one or more of the balls;

wherein the training module is further configured to electronically submit the player training data over a network to a soccer network application along with a request for feedback from a remote coach through the soccer network application, and in response to said submitting the training session data, receive a customized training program from the coach via the soccer network application, the customized training program comprising one or more second drills to be executed by the soccer ball throwing device.

\* \* \* \* \*

UNITED STATES PATENT AND TRADEMARK OFFICE
CERTIFICATE OF CORRECTION

| | | |
|---|---|---|
| PATENT NO. | : 9,010,309 B2 | Page 1 of 1 |
| APPLICATION NO. | : 13/287749 | |
| DATED | : April 21, 2015 | |
| INVENTOR(S) | : Edward J. Lewis et al. | |

It is certified that error appears in the above-identified patent and that said Letters Patent is hereby corrected as shown below:

In the specification

In column 18 at line 7, Change "all together" to --altogether--.

In the claims

In column 22 at line 5 (approx.), Change "comprising" to --comprising:--.

Signed and Sealed this
Seventeenth Day of May, 2016

Michelle K. Lee
*Director of the United States Patent and Trademark Office*